United States Patent [19]
Modlin et al.

[11] Patent Number: 6,071,748
[45] Date of Patent: Jun. 6, 2000

[54] LIGHT DETECTION DEVICE

[75] Inventors: Douglas N. Modlin; Glenn R. Edwards, both of Palo Alto; Michael T. Taylor, Newark; Samuel A. Marquiss, Santa Clara, all of Calif.

[73] Assignee: LJL BioSystems, Inc., Sunnyvale, Calif.

[21] Appl. No.: 09/062,472

[22] Filed: Apr. 17, 1998

Related U.S. Application Data

[60] Provisional application No. 60/052,876, Jul. 16, 1997, provisional application No. 60/059,639, Sep. 20, 1997, provisional application No. 60/063,811, Oct. 31, 1997, provisional application No. 60/072,499, Jan. 26, 1998, provisional application No. 60/072,780, Jan. 27, 1998, provisional application No. 60/075,806, Feb. 24, 1998, provisional application No. 60/075,414, Feb. 20, 1998, and provisional application No. 60/082,253, Apr. 17, 1998.

[51] Int. Cl.[7] .................................................. G01N 21/01
[52] U.S. Cl. ............................ 436/174; 436/43; 436/164; 436/807; 436/809; 422/63; 422/65; 422/82.05; 422/82.08; 422/104; 422/52; 250/459.1; 250/491.1; 356/317; 356/318; 356/417
[58] Field of Search ........................... 636/43, 68, 50, 636/164, 174, 805, 807, 809; 422/63, 65, 67, 82.05, 82.08, 52, 102, 104; 356/317, 318, 417; 250/458.1, 459.1, 461.1, 461.2, 428, 432 R, 491.1

[56] References Cited

U.S. PATENT DOCUMENTS 2,719,214 9/1955 Potter .
3,013,467 12/1961 Minsky .

(List continued on next page.)

FOREIGN PATENT DOCUMENTS

| 0 266 881 A2 | 5/1988 | European Pat. Off. . |
|---|---|---|
| 2 215 838 | 9/1989 | United Kingdom . |
| 2 228 081 | 8/1990 | United Kingdom . |

OTHER PUBLICATIONS

*Fundamentals of Light Microscopy,* Spencer, Cambridge University Press, 1982.
Basic Fluorescence Microscopy, Taylor et al., *Methods on Cell Biology,* vol. 29, pp. 207–237, 1989.
Quantitative Fluorescence Microscopy Using Photomultiplier Tubes and Imaging Detectors, Wampler et al., *Methods in Cell Biology,* vol. 29, pp. 239–267, 1989.
Three–Dimensional Confocal Fluorescence Microscopy, Brakenhoff et al., *Methods in Cell Biology,*vol. 30, pp. 379–389, 1989.
Laser Scanning Confocal Microscopy of Living Cells, Lemasters et al., *Optical Microscopy: Emerging Methods and Applications,*pp. 339–345, 1993.
Time–Resolved Fluorescence Lifetime Imaging, vandeVen et al., *Optical Microscopy: Emerging Methods and Applications,* pp. 373–389, 1993.
Tecan SPECTRAfluor—A Step Forward in Microplate Fluorometry, internet description pages, Jun. 17, 1998.
Wallac Time–Resolved Fluorometry'The Key to Improved Assay Sensitivity, internet description pages, Jul. 7, 1998.
Wallac 1234 DELFIA Fluorometer, internet description page, Jul. 7, 1998.
Wallac 1420 Victor Multilabel Counter, internet description pages, Jul. 7, 1998.
Wallac 1420 Victor[2] Multilabel Counter, internet description pges, Jul. 7, 1998.
Wallac 1442 Arthur Multi–Wavelength Fluoroimager, internet description page, Jul. 7, 1998.
Wallac Labelling Reagents for Time–Resolved Fluorometry, internet description page, Jul. 7, 1998.

*Primary Examiner*—Long V. Le
*Attorney, Agent, or Firm*—Kolisch, Hartwell, Dickinson, McCormack & Heuser

[57] ABSTRACT

A high-throughput light detection instrument and method are described. Confocal optics structure enables exclusive light detection from a sensed volume in a composition.

77 Claims, 18 Drawing Sheets

U.S. PATENT DOCUMENTS

| | | |
|---|---|---|
| 3,423,581 | 1/1969 | Baer . |
| 3,516,736 | 6/1970 | Weaver . |
| 3,849,654 | 11/1974 | Malvin . |
| 3,932,023 | 1/1976 | Humer . |
| 4,011,451 | 3/1977 | Nelson . |
| 4,067,653 | 1/1978 | Fletcher et al. . |
| 4,076,420 | 2/1978 | De Maeyer et al. . |
| 4,100,416 | 7/1978 | Hirschfeld . |
| 4,144,452 | 3/1979 | Harte . |
| 4,150,870 | 4/1979 | d'Auria . |
| 4,203,670 | 5/1980 | Bromberg . |
| 4,341,957 | 7/1982 | Wieder . |
| 4,451,149 | 5/1984 | Noeller . |
| 4,485,430 | 11/1984 | Achiaga Fustel . |
| 4,501,970 | 2/1985 | Nelson . |
| 4,567,847 | 2/1986 | Linner . |
| 4,626,684 | 12/1986 | Lander . |
| 4,685,801 | 8/1987 | Minekane . |
| 4,699,512 | 10/1987 | Koshi . |
| 4,704,255 | 11/1987 | Jolley . |
| 4,707,067 | 11/1987 | Haberland et al. . |
| 4,724,217 | 2/1988 | Miller . |
| 4,730,921 | 3/1988 | Klein et al. . |
| 4,738,825 | 4/1988 | Kelln et al. ............................... 422/72 |
| 4,741,619 | 5/1988 | Humphries et al. . |
| 4,753,501 | 6/1988 | Battle . |
| 4,762,420 | 8/1988 | Bowley . |
| 4,772,453 | 9/1988 | Lisenbee . |
| 4,784,275 | 11/1988 | Fridge . |
| 4,810,096 | 3/1989 | Russell et al. . |
| 4,826,660 | 5/1989 | Smith et al. . |
| 4,855,930 | 8/1989 | Chao et al. . |
| 4,868,103 | 9/1989 | Starvrianopoulos et al. . |
| 4,873,633 | 10/1989 | Mezei et al. . |
| 4,877,965 | 10/1989 | Dandliker et al. . |
| 4,885,087 | 12/1989 | Kopf . |
| 4,892,409 | 1/1990 | Smith . |
| 4,923,819 | 5/1990 | Fernandez et al. . |
| 4,936,682 | 6/1990 | Hoyt . |
| 4,948,442 | 8/1990 | Manns . |
| 4,968,148 | 11/1990 | Chow et al. . |
| 4,979,821 | 12/1990 | Schutt et al. . |
| 5,009,488 | 4/1991 | Fay et al. . |
| 5,039,219 | 8/1991 | James et al. . |
| 5,047,215 | 9/1991 | Manns . |
| 5,058,045 | 10/1991 | Ma . |
| 5,082,628 | 1/1992 | Andreotti et al. . |
| 5,084,246 | 1/1992 | Lyman et al. . |
| 5,091,652 | 2/1992 | Mathies et al. . |
| 5,095,517 | 3/1992 | Monguzzi et al. . |
| 5,096,807 | 3/1992 | Leaback . |
| 5,169,601 | 12/1992 | Ohta et al. . |
| 5,192,510 | 3/1993 | Zoha et al. . |
| 5,206,568 | 4/1993 | Bjornson et al. . |
| 5,208,161 | 5/1993 | Saunders et al. . |
| 5,208,651 | 5/1993 | Buican . |
| 5,225,164 | 7/1993 | Astle . |
| 5,257,202 | 10/1993 | Feddersen et al. . |
| 5,270,788 | 12/1993 | Cercek et al. . |
| 5,273,718 | 12/1993 | Skold et al. ............................ 422/101 |
| 5,275,951 | 1/1994 | Chow et al. . |
| 5,315,015 | 5/1994 | Hui et al. . |
| 5,317,485 | 5/1994 | Merjanian . |
| 5,319,436 | 6/1994 | Manns et al. . |
| 5,323,008 | 6/1994 | Studholme et al. . |
| 5,340,716 | 8/1994 | Ullman et al. . |
| 5,340,747 | 8/1994 | Eden . |
| 5,355,215 | 10/1994 | Schroeder et al. . |
| 5,361,626 | 11/1994 | Colligan et al. . |
| 5,384,093 | 1/1995 | Ootani et al. . |
| 5,401,465 | 3/1995 | Smethers et al. . |
| 5,418,371 | 5/1995 | Aslund et al. . |
| 5,420,408 | 5/1995 | Weyrauch et al. . |
| 5,436,718 | 7/1995 | Fernandes et al. . |
| 5,445,935 | 8/1995 | Royer . |
| 5,449,921 | 9/1995 | Baba . |
| 5,457,527 | 10/1995 | Manns et al. . |
| 5,459,300 | 10/1995 | Kasman . |
| 5,480,804 | 1/1996 | Niwa et al. . |
| 5,485,530 | 1/1996 | Lakowicz et al. . |
| 5,487,872 | 1/1996 | Hafeman et al. . |
| 5,491,343 | 2/1996 | Brooker . |
| 5,512,492 | 4/1996 | Herron et al. . |
| 5,528,046 | 6/1996 | Ishikawa . |
| 5,537,343 | 7/1996 | Kikinis et al. . |
| 5,542,012 | 7/1996 | Fernandes et al. . |
| 5,557,398 | 9/1996 | Wechsler et al. . |
| 5,589,136 | 12/1996 | Northrup et al. . |
| 5,589,350 | 12/1996 | Bochner . |
| 5,589,351 | 12/1996 | Harootunian . |
| 5,592,289 | 1/1997 | Norris . |
| 5,593,867 | 1/1997 | Walker et al. . |
| 5,595,710 | 1/1997 | Van Dusen et al. . |
| 5,599,500 | 2/1997 | Jones . |
| 5,604,130 | 2/1997 | Warner et al. . |
| 5,620,894 | 4/1997 | Barger et al. . |
| 5,626,134 | 5/1997 | Zuckerman . |
| 5,631,734 | 5/1997 | Stern et al. . |
| 5,633,724 | 5/1997 | King et al. . |
| 5,635,402 | 6/1997 | Alfano et al. . |
| 5,641,633 | 6/1997 | Linn et al. . |
| 5,663,545 | 9/1997 | Marquiss . |
| 5,676,943 | 10/1997 | Baetge et al. . |
| 5,679,310 | 10/1997 | Manns . |
| 5,736,410 | 4/1998 | Zarling et al. ........................... 436/172 |
| 5,780,857 | 7/1998 | Harju et al. . |
| 5,825,617 | 10/1998 | Kochis et al. . |
| 5,842,582 | 12/1998 | DeStefano, Jr. . |

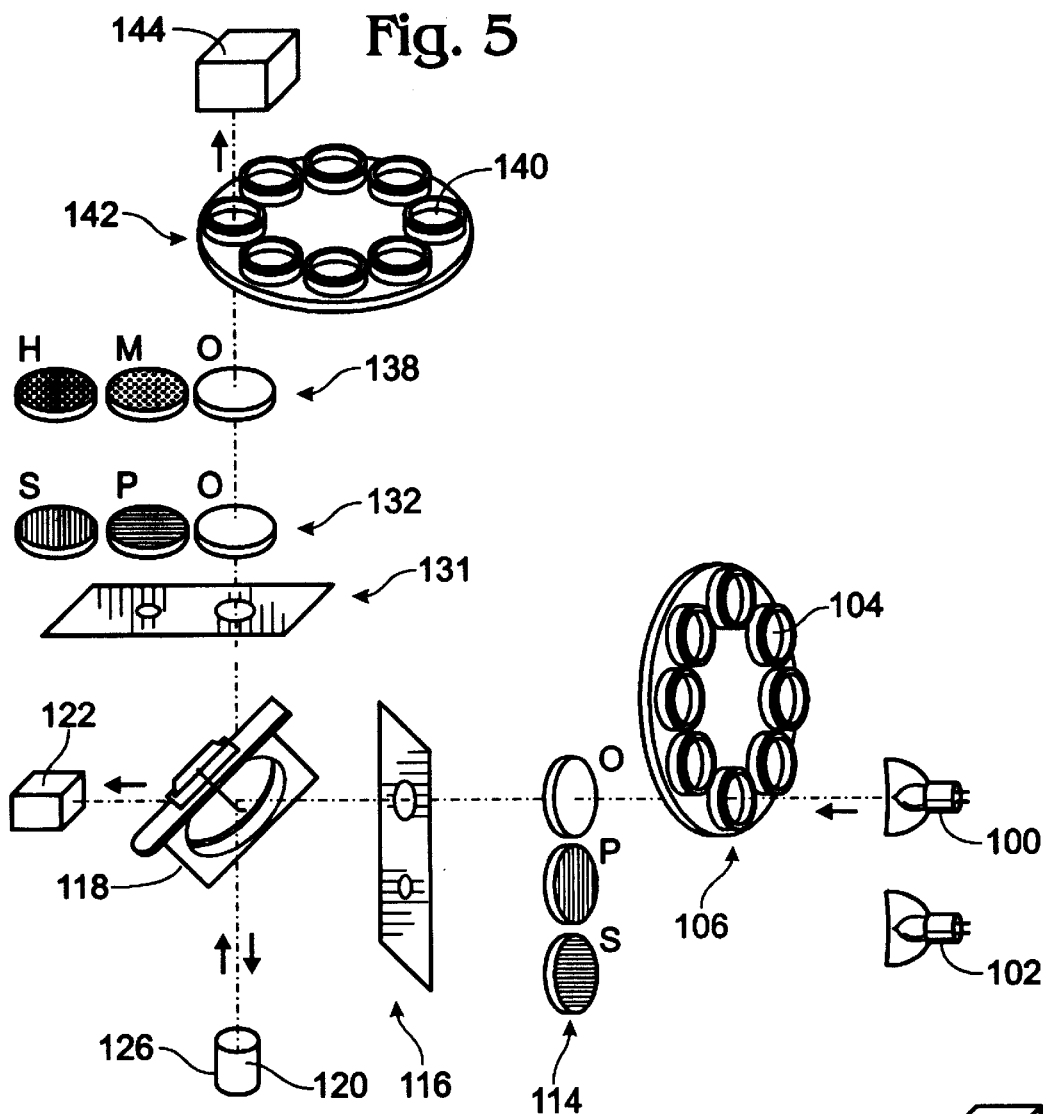
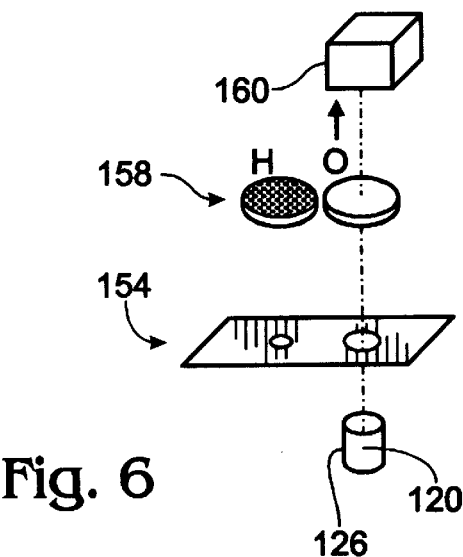

A  B  C  D

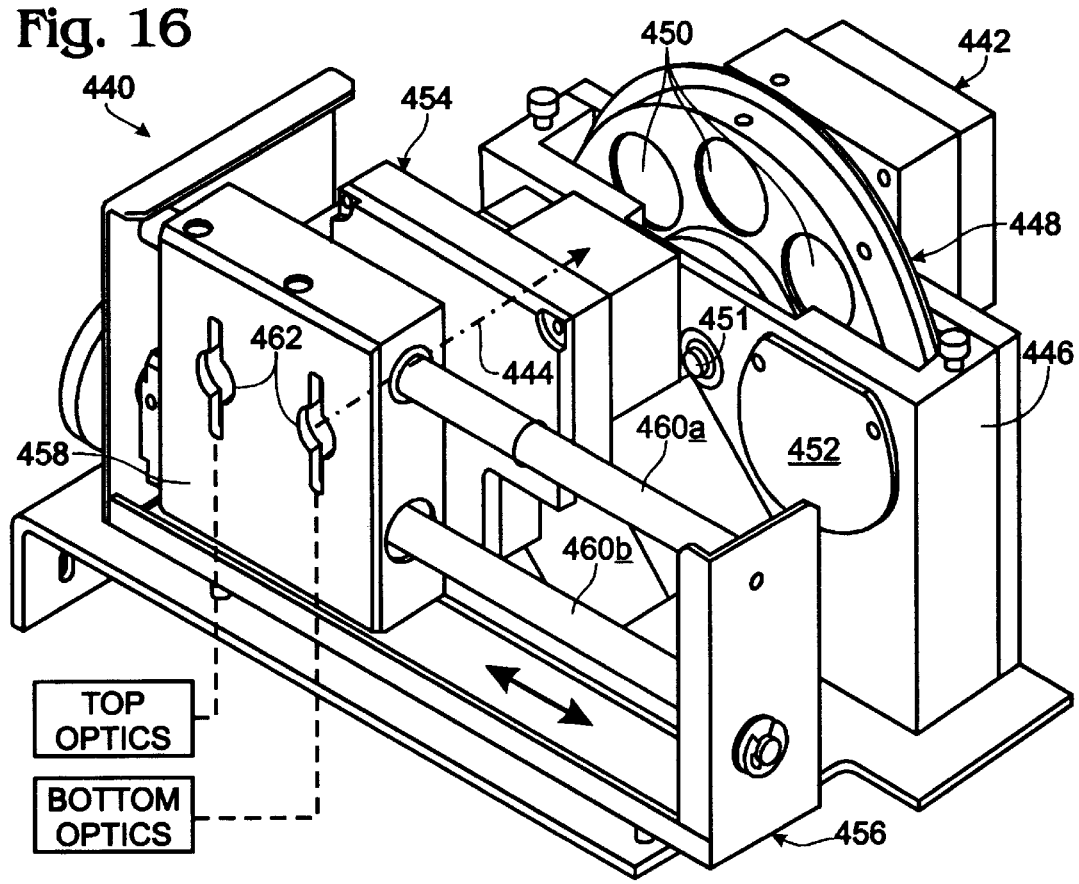

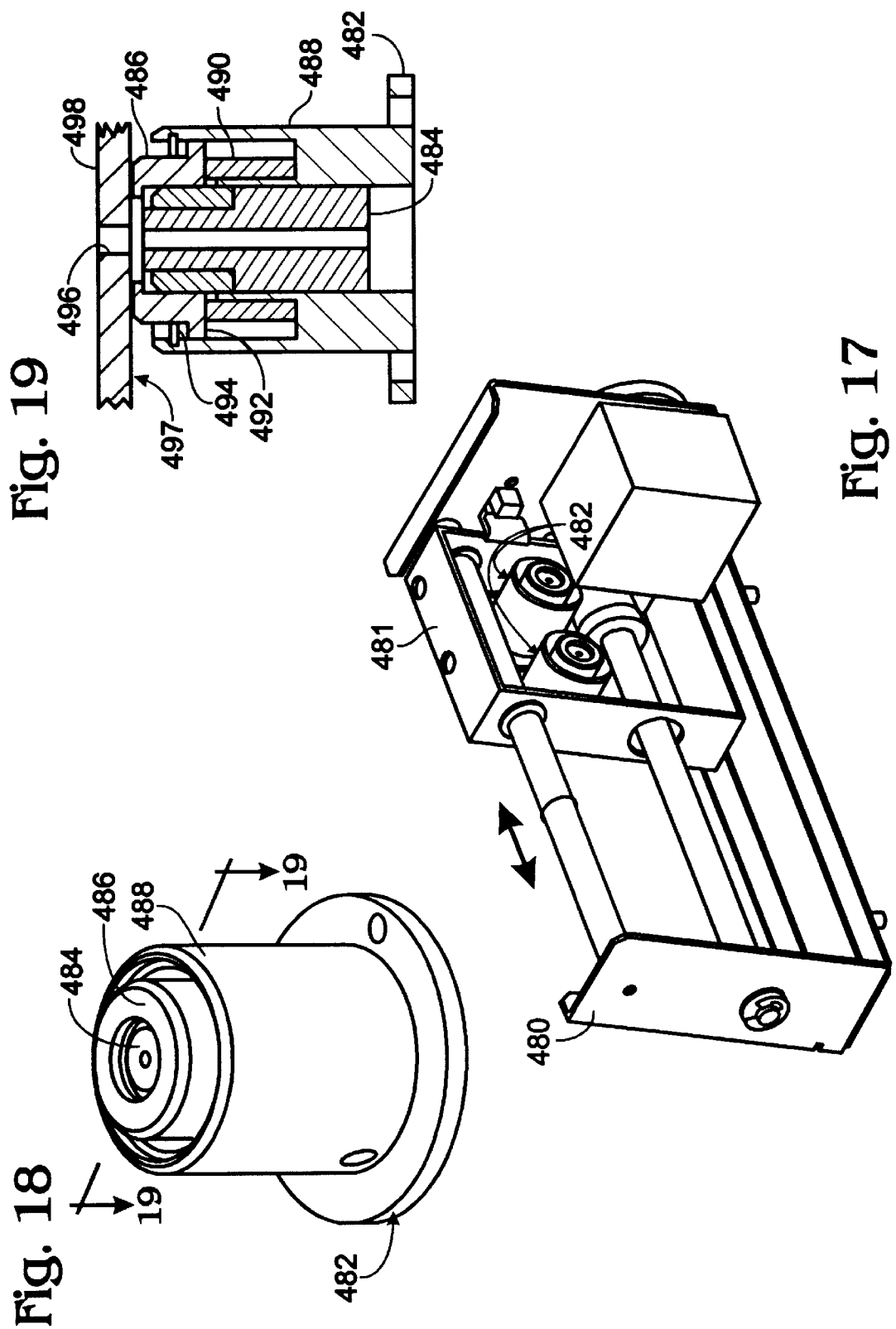

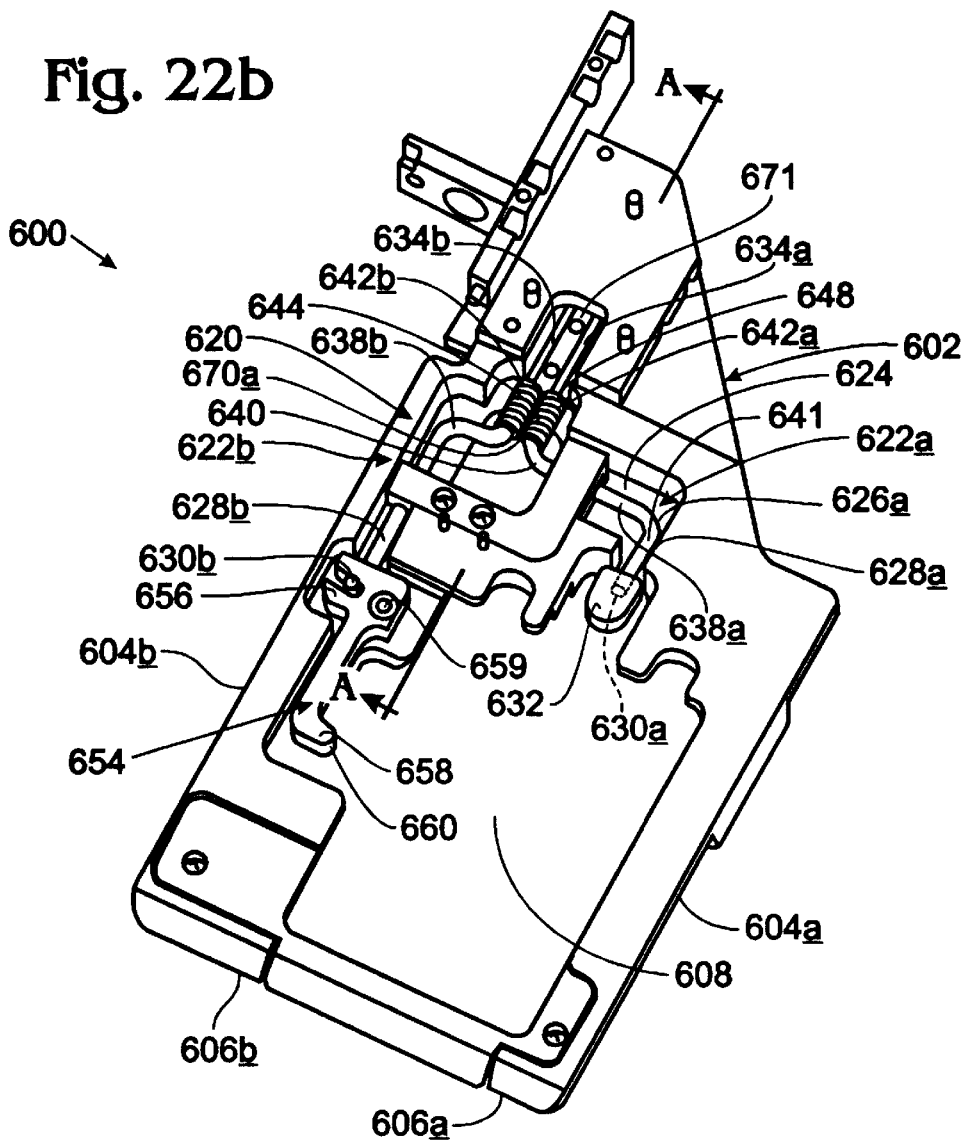

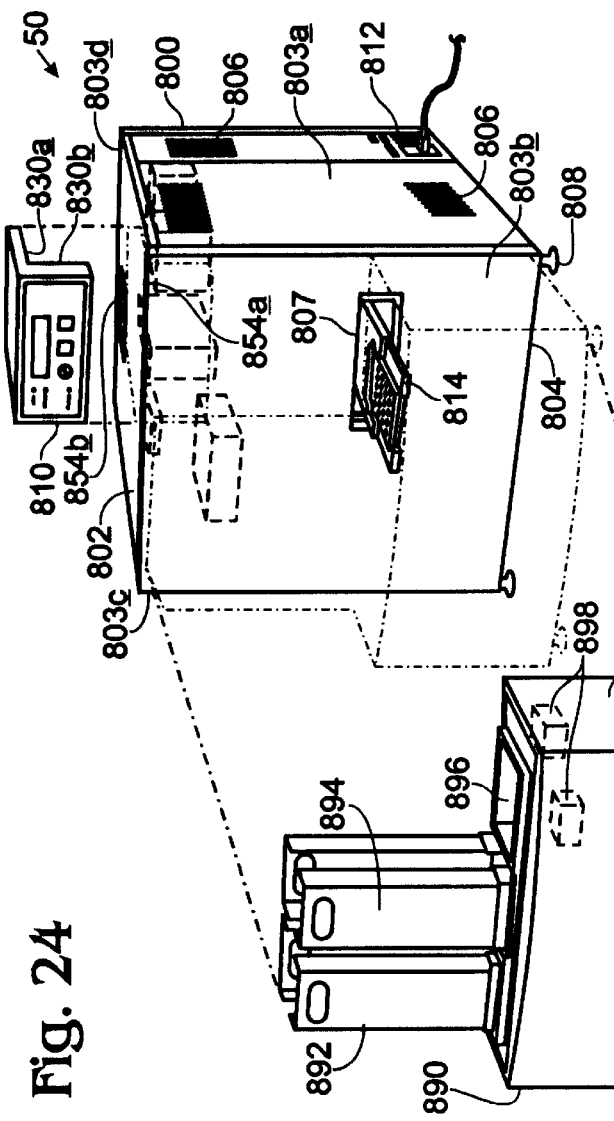
Fig. 24
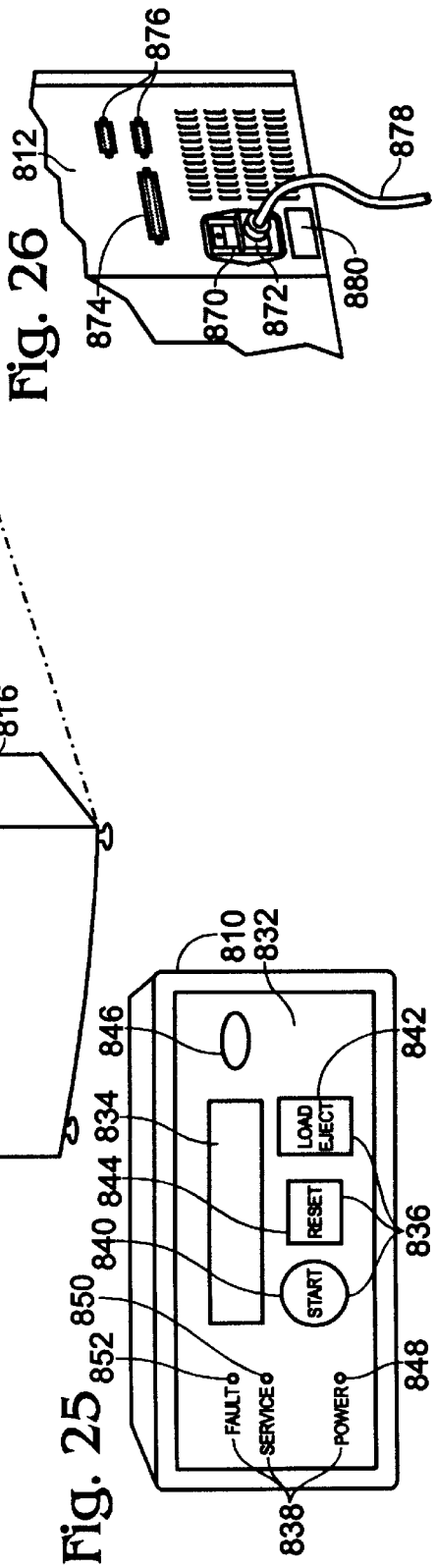
Fig. 25
Fig. 26

LIGHT DETECTION DEVICE

CROSS-REFERENCE TO RELATED APPLICATIONS

This application is based upon and claims benefit under 35 U.S.C. § 119 of the following U.S. Provisional Patent Applications, each of which is incorporated herein by reference: Ser. No. 60/052,876, filed Jul. 16, 1997; Ser. No. 60/059,639, filed Sep. 20, 1997; Ser. No. 60/063,811, filed Oct. 31, 1997; Ser. No. 60/072,499, filed Jan. 26, 1998; Ser. No. 60/072,780, filed Jan. 27, 1998; Ser. No. 60/075,806, filed Feb. 24, 1998; Ser. No. 60/075,414, filed Feb. 20, 1998; and Ser. No. 60/082,253, filed Apr. 17, 1998, titled LIGHT DETECTION DEVICE, and naming Douglas N. Modlin, Glenn R. Edwards, Michael T. Taylor, and Samuel A. Marquiss as inventors.

FIELD OF THE INVENTION

The invention relates to instrumentation and methods for detecting light. In particular, the invention relates to a versatile, sensitive, high-throughput screening apparatus that quantifies light transmitted from an assay site.

BACKGROUND OF THE INVENTION

High-throughput screening instruments are critical tools in the pharmaceutical research industry and in the process of discovering and developing new drugs. The drug discovery process involves synthesis and testing, or screening, of candidate drug compounds against a target. A candidate drug compound is a molecule that might mediate a disease by its effect on a target. A target is a biological molecule, such as an enzyme, receptor, other protein, or nucleic acid, that is believed to play a role in the onset or progression of a disease or a symptom of a disease. FIG. 1 shows stages of the drug discovery process, which include target identification, compound synthesis, assay development, screening, secondary screening of hits, and lead compound screening, or optimization, and finally clinical evaluation.

Targets are identified based on their anticipated role in the progression or prevention of a disease. Until recently, scientists using conventional methods had identified only a few hundred targets, many of which have not been comprehensively screened. Recent developments in molecular biology and genomics have led to a dramatic increase in the number of targets available for drug discovery research.

After a target is selected, a library of compounds is selected to screen against the target. Compounds historically have been obtained from natural sources or synthesized one at a time. Compound libraries were compiled over decades by pharmaceutical companies using conventional synthesis techniques. Recent advances in combinatorial chemistry and other chemical synthesis techniques, as well as licensing arrangements, have enabled industrial and academic groups greatly to increase the supply and diversity of compounds available for screening against targets. As a result, many researchers are gaining access to libraries of hundreds of thousands of compounds in months rather than years.

Following selection of a target and compound library, the compounds must be screened to determine their effect on the target, if any. A compound that has an effect on the target is defined as a hit. A greater number of compounds screened against a given target results in a higher statistical probability that a hit will be identified.

Prior to screening compounds against a target, a biological test or assay must be developed. An assay is a combination of reagents that is used to measure the effect of a compound on the activity of a target. Assay development involves selection and optimization of an assay that will measure performance of a compound against the selected target. Assays are broadly classified as either biochemical or cellular. Biochemical assays usually are performed with purified molecular targets, which generally have certain advantages, such as speed, convenience, simplicity, and specificity. Cellular assays are performed with living cells, which may sacrifice speed and simplicity, but which may provide more biologically relevant information. Researchers use both biochemical and cellular assays in drug discovery research. Both types of assays may use a variety of detection modalities, including absorbance, radioisotopic, chemiluminescence, and photoluminescence.

Assays are then run to identify promising compound candidates or hits. Once a compound is identified as a hit, a number of secondary screens are performed to evaluate its potency and specificity for the intended target. This cycle of repeated screening continues until a small number of lead compounds are selected. The lead compounds are optimized by further screening. Optimized lead compounds with the greatest therapeutic potential may be selected for clinical evaluation.

Due to the recent dramatic increase in the number of available compounds and targets, a bottleneck has resulted at the screening stage of the drug discovery process. Historically, screening has been a manual, time-consuming process. Screening significantly larger numbers of compounds against an increasing number of targets requires a system that can operate with a high degree of automation, analytical flexibility, and speed.

The most common high-throughput screening assay techniques utilize absorbance, radio-isotope labeling, photoluminescence (e.g., fluorescence) intensity, photoluminescence (e.g., fluorescence) polarization, and time resolved fluorescence (e.g., phos-fluorescence). There is a desire in the high-throughput screening industry to provide alternatives to assays that use radio-isotopes because: (1) radio-isotopes are relatively expensive and there is a question as to how well they will perform at low volumes, (2) they pose potential health hazards to workers, and (3) their disposal is problematic. In contrast, photoluminescence and chemiluminescence-based assays generally are attractive because they offer a sensitive assay read-out capability that is significantly less problematic for workers and much easier to dispose of than radio-isotopes.

The types of assays that are desired for high-throughput screening are evolving constantly. As new assays are developed in research labs, tested, and published in literature or presented at scientific conferences, new assays become popular and many become available commercially. New analytical equipment then is developed to support the most popular commercially available assays.

Current screening systems operate with various degrees of automation. Automation, from sample dispensing to data collection, enables round-the-clock operation, thereby increasing the screening rate. Automated high-throughput screening systems usually include combinations of assay analyzers, liquid handling systems, robotics, computers for data management, reagents and assay kits, and microplates.

Most analyzers in use today offer only a single assay modality or a limited set of modalities with non-optimum peirfomance. To perform assays using different detection modes, researchers generally must switch single-mode analyzers and reconfigure the high-throughput screening line.

Alternatively, researchers may set up the high-throughput screening line with multiple single-mode analyzers, which often results in critical space constraints.

Most analyzers used today are not designed specifically for high-throughput screening purposes. They are difficult and expensive to integrate into a high-throughput screening line. Even after the analyzer is integrated into the high-throughput screening line, there often are many problems, including increased probability of system failures, loss of data, time delays, and loss of costly compounds and reagents.

The proliferation of targets and compounds to be screened has given rise to the need to conserve reagents in order to reduce total screening costs. However, detection systems in use today generally are not designed to permit significant reduction in assay volume, as evidenced by the need to run microplates with completely filled wells and high reporter group concentrations in order to achieve acceptable performance. Many analyzers are not sensitive enough to read results based on these smaller volumes. Inadequate sensitivity may result in missed hits, limited research capabilities, increased costs of compounds, assays, and reagents, and lower throughput.

Ninety-six-well microplate formats have been and still are commonly used throughout the high-throughput screening industry. Some high-throughput screening labs are using 384- and 768-well plates, and some labs are experimenting with 1536-, 3456-, and 9600-well microplates. FIG. 2 shows a stack of overlapping microplates with various well densities. Plate 30 has 96 wells. Plate 32 has 384 wells. Plate 34 has 1536 wells. Plate 36 has 3456 wells. Plate 38 has 9600 wells. FIG. 2 illustrates the substantial difference in well dimensions and densities that may be used in high-throughput screening assays.

The need for flexibility to handle various microplate well densities presents significant challenges because reduction in sample volume may sacrifice sensitivity and because light interaction at sample boundary interfaces, including those defined by container walls, often contributes significant background noise, causing losses in the signal-to-noise ratio, as different container densities, capacities, and geometries are used.

In addition to differences in well density and capacity, well geometries are highly variable. Well side walls vary, For example, some side walls are horizontal, whereas others are slanted. Well bottoms also vary. For example, some well bottoms are flat, whereas others are V-shaped or U-shaped. Well peripheral shapes also vary. For example, some well peripheral shapes are round, whereas others are square or hexagonal. Some wells have baffles for mixing or for increasing surface area. Each of these variations presents different potential interfacial boundary interference problems.

The problem of handling different sample volumes and container geometries is further complicated by other high-throughput screening objectives, such as the goal of offering multi-mode detection and assay variability. Interference from light interaction at interfacial boundaries around the sample may cause more of a problem for one type of assay compared to another. Consequently, inability to avoid, or at least manage, interference due to variations in container density, shape, and size inevitably imposes limitations on the assay flexibility of a given analyzer. It may be necessary to use sample containers of standard dimension, and it may be necessary to provide different analyzers for different modes of analysis.

Thus, prior detection devices have not generally recognized the need to provide analytic flexibility and high performance for assay development as well as ease of use and smooth automation interface for the high-throughput screening lab. A real need exists for a sensitive, versatile, multi-mode analyzer with high-throughput capability that can handle wide ranges of sample volumes and variations in container material, geometry, size and density format while reliably maintaining a high level of sensitivity.

SUMMARY OF THE INVENTION

The present invention provides an apparatus and method for detecting light transmitted from a composition. The apparatus includes a stage for supporting a composition in an examination site, where the composition is contained in a spatial volume lying between boundary interfaces located at different points along a Z-axis, perpendicular to the stage. An automated registration device automatically brings successive compositions and the examination site into register for analysis. A light source is positioned to deliver light to the composition in the examination site. A detector is positioned to receive light transmitted from the composition in the examination site. An optical relay structure is located between the light source and the detector. The optical relay structure transmits light substantially exclusively from a sensed volume of the composition. The sensed volume is spaced substantially away from at least one of the boundary interfaces of the composition.

In a preferred embodiment, the optical relay structure employs a confocal optical system. A first aperture and a first lens are positioned along a light path between the light source and the examination site, or between the detector and the examination site. The first aperture and the first lens are contained in a first optics head positioned above the stage. The first optics head has a light entrance port optically connected to the light source and a light exit port optically connected to the detector, so that illumination and detection of light transmitted from a composition in the examination site can be carried out from the same side of the stage. The light entrance port and the light exit port each transmit light in directions that are substantially perpendicular to each other. The optics head also includes a planar beamsplitter oriented at 45-degree angles to the directions of light transmission.

A similar second optics head may be positioned below the stage. Each optics head has a light entrance port optically connected to the light source, and a light exit port optically connected to the detector. A switch control mechanism provides the capability of interchangeably configuring any one of the following light transmission routes to and from a sensed volume in a composition located at the examination site: (a) top-illumination and top-detection, (b) top-illumination and bottom-detection, (c) bottom-illumination and top-detection, and (d) bottom-illumination and bottom-detection.

The invention also provides a method of detecting light transmitted from a composition. A first step is callied out by automatically bringing into register a succession of compositions at an examination site for analysis. Each composition is contained between top and bottom boundary interfaces. A second step involves transmitting light into a composition at the examination site. Detection of transmitted light is carried out substantially exclusively from a sensed volume of the composition that is spaced substantially away from at least one of the boundary interfaces.

BRIEF DESCRIPTION OF THE FIGURES

FIG. 5 is a schematic view of optical components of an embodiment of the invention.

FIG. 6 is a schematic view of components of a chemiluminescence optical system of the present invention.

FIG. 16 is a partial perspective, partial schematic view of a detector module employed in a preferred embodiment of the present invention.

FIG. 17 is a partial perspective view of a fiber optics shuttle assembly used in an embodiment of the invention.

FIG. 18 is a perspective view of a floating head assembly used in the fiber optic shuttle assembly shown in FIG. 17.

FIG. 19 is a cross-sectional view of the floating head assembly shown in FIG. 18.

FIG. 22b is a bottom view of the transporter assembly shown in FIG. 22a.

FIG. 22c is a partial cross-sectional view of the transporter assembly shown in FIG. 22b.

FIG. 24 is a perspective, partially exploded, view of a housing for an analyzer of the present invention.

FIG. 25 is a front view of the control panel shown in FIG. 24.

FIG. 26 is a front view of the input/output panel shown in FIG. 24.

DETAILED DESCRIPTION OF THE INVENTION

Figure 1:
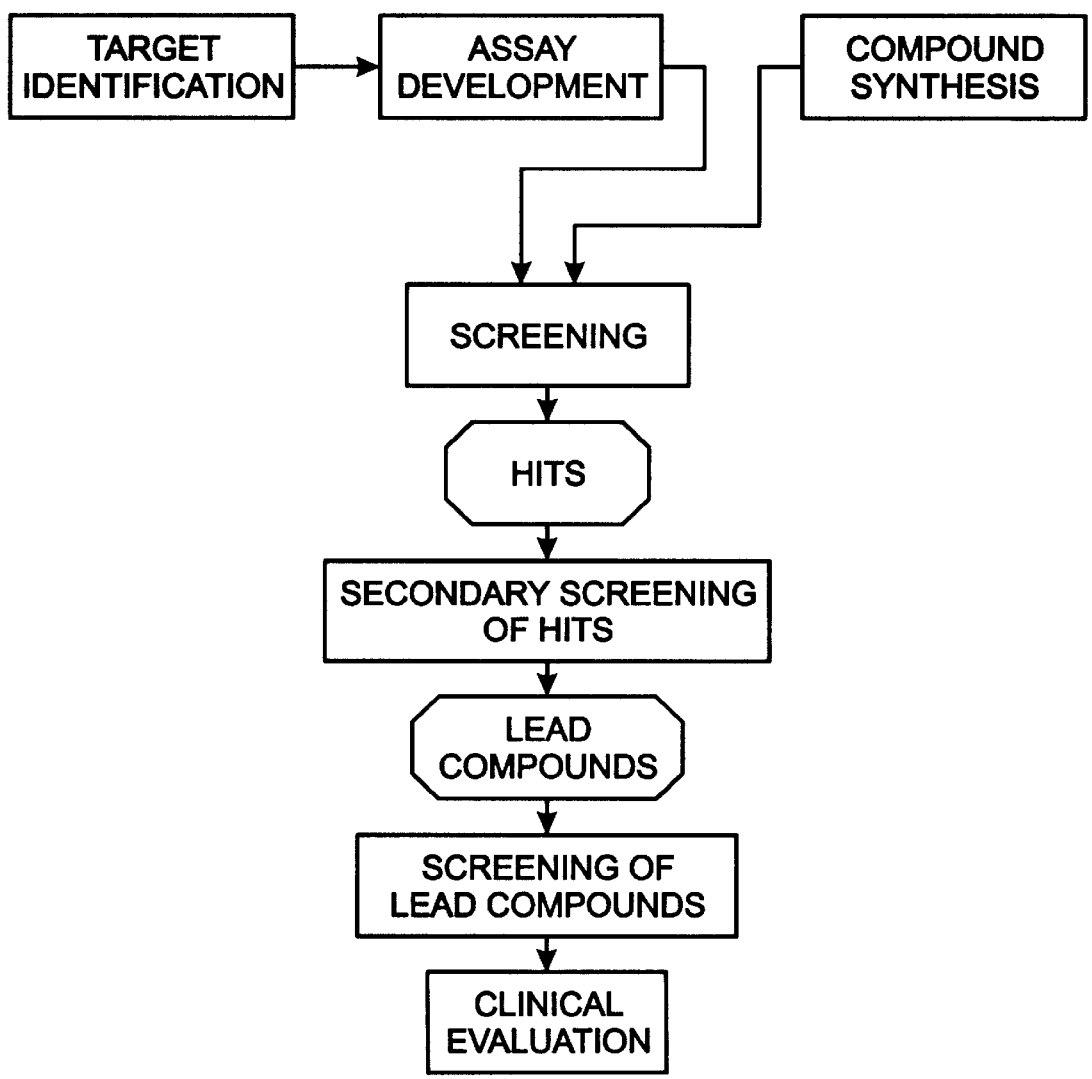
FIG. 1 is a flow chart showing elements of the drug discovery process.
Figure 2:
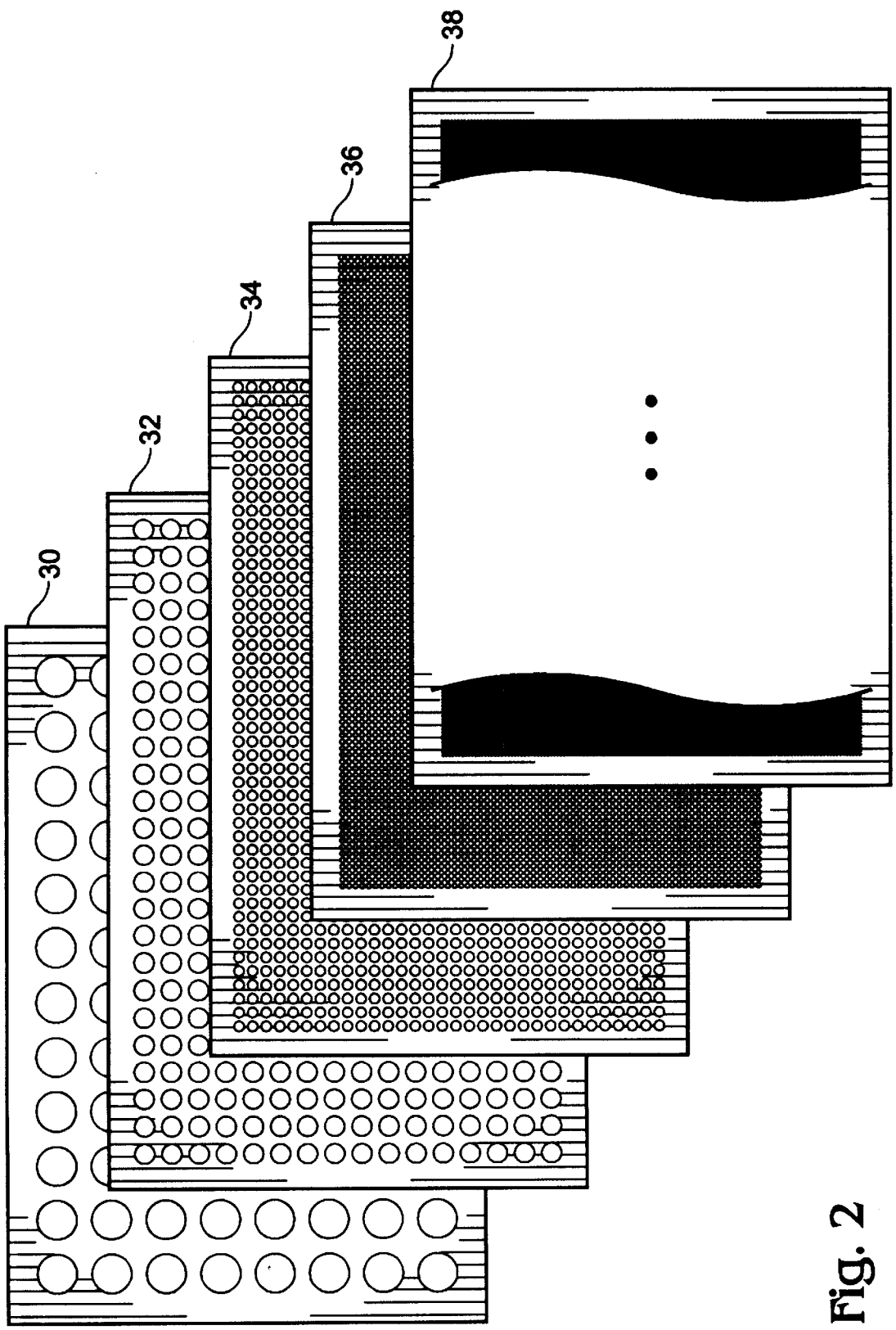
FIG. 2 is a top view of overlapping microplates illustrating variations in well density.

The invention provides an analyzer that enables a wide range of assay formats which can be carefully selected and fine-tuned for screening desired targets with acceptable quality and reliability, while also allowing assays to be run in smaller containers with reduced volumes. The analyzer achieves these objectives, in part, by employing an optical system that minimizes sample interfacial boundary interference, thereby permitting reduction in assay volume in existing fortnats such as 96 or 384 well plates, and utilization of denser formats such as 768, 1536, 3456, or 9600 well plates. The analyzer also enables assay flexibility by providing the capability of automatically switching between different modes, including photoluminescence, photoluminescence polarization, time-resolved photoluminescence, photoluminescence lifetime, and chemiluminescence modalities.

The apparatus of the present invention generally includes a stage for supporting a composition in an examination site, an automated registration device for bringing successive compositions and the examination site into register for analysis of the compositions, a light source for delivering light into the compositions, a detector for receiving light transmitted from the compositions, and an optical relay structure for transmitting light substantially exclusively from a sensed volume that may comprise only a portion of the composition.

The analyzer is designed to be flexible, durable, and convenient. Flexibility means that it can be used with a variety of samples and sample assays. Durability means that it can be used repeatedly, at high throughput, in laboratory and industrial settings. Convenient means that it can be used with only minimal user intervention.

Description of the Optical System

FIGS. 3–6 show a preferred embodiment of the optical system of an analyzer 50 constructed in accordance with the present invention. The optical system generally includes at least one light source for delivering light to a composition, at least one detector for receiving light transmitted from the composition, and an optical relay structure for relaying light between the light source, composition, and detector, and for limiting detection to a sensed volume that may comprise only a portion of the composition.

Components of the optical system are chosen to optimize sensitivity and dynamic range for each assay mode supported by the analyzer. Toward this end, optical components with low intrinsic luminescence are chosen. In addition, some components are shared by different modes, whereas other components are unique to a particular mode. For example, photoluminescence intensity and steady-state photoluminescence polarization modes share a light source; time-resolved luminescence modes use their own light source; and chemiluminescence modes do not use a light source. Similarly, photoluminescence and chemiluminescence modes use different detectors.

These assay modes all involve detection of luminescence, which is the emission of light from excited electronic states of atoms or molecules. Luminescence generally refers to all kinds of light emission, except incandescence, and may include photoluminescence, chemiluminescence, and electrochemiluminescence, among others. In photoluminescence, including fluorescence and phosphorescence, the excited electronic state is created by the absorption of electromagnetic radiation. In chemiluminescence, the excited electronic state is created by a transfer of chemical energy. In electrochemiluminescence, the excited electronic state is created by an electrochemical process.

Separate descriptions of the photoluminescence and chemiluminescence optical systems are presented below. Selected components of both systems are described in greater detail in subsequent sections. The optical system presented here is a preferred embodiment. The present invention also includes other arrangements and components capable of detecting light from a sensed volume in higlhthlrouglhput applications.

Figure 3:
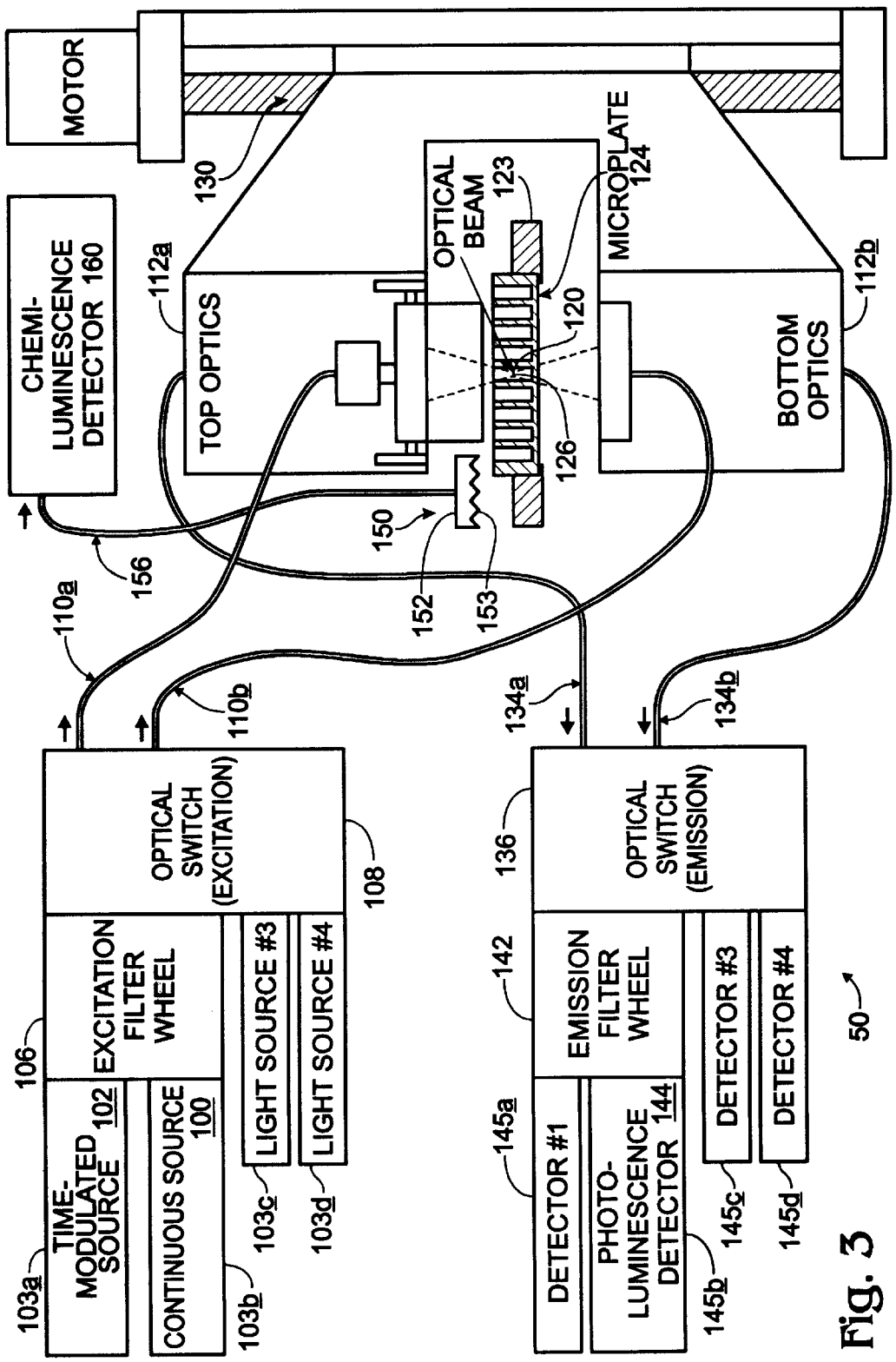
FIG. 3 is a schematic view of analyzer components according to a preferred embodiment of the invention.
Figure 4:
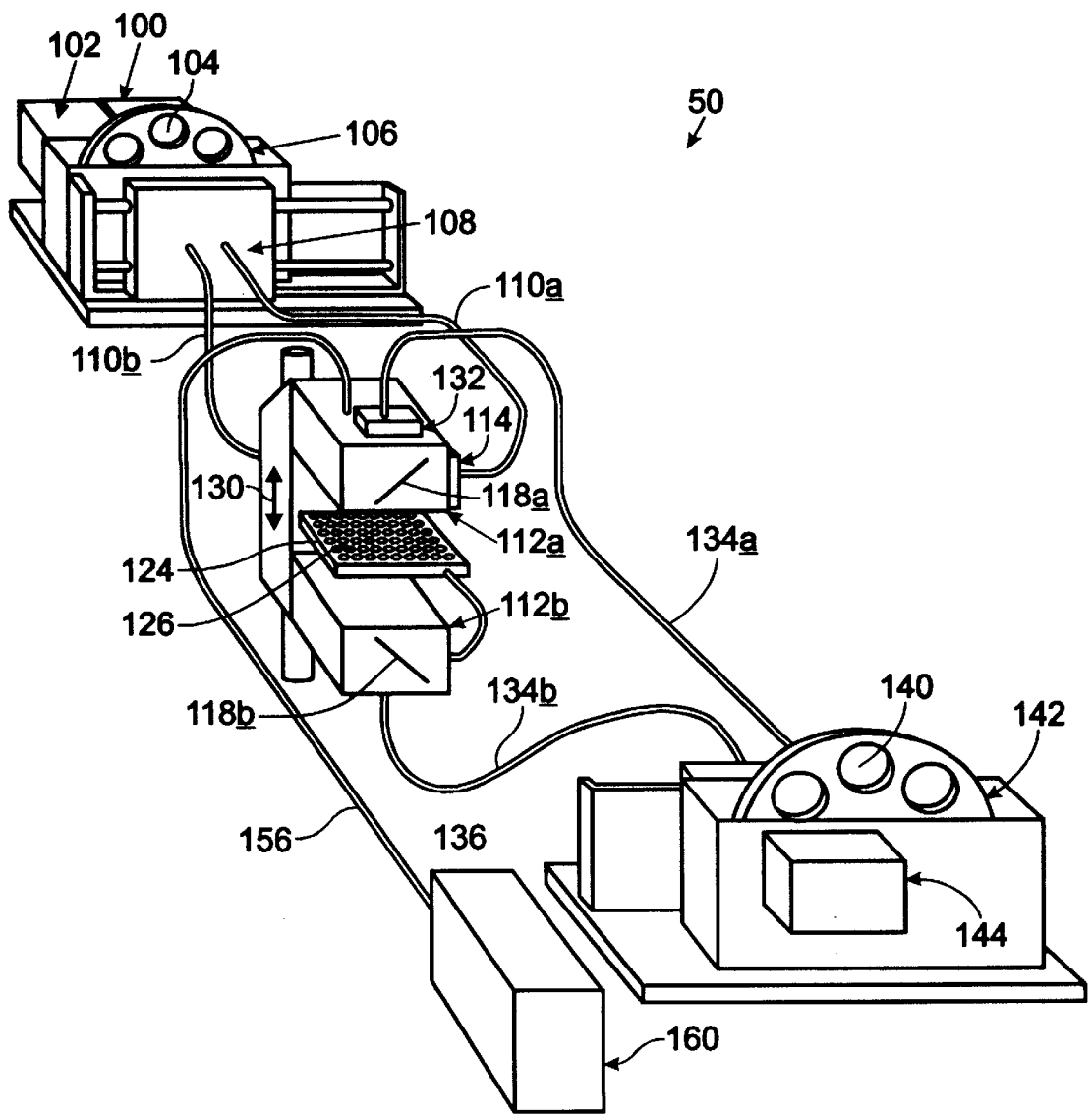
FIG. 4 is a schematic, partial perspective view of analyzer components.

Photoluminescence optical system. FIGS. 3–5 show the photoluminescence optical system of analyzer 50. Because photoluminescence follows the absorption of light, the photoluminescence optical system must include one or more light sources. In analyzer 50, there are two light sources. A continuous source 100 provides light for photoluminescence intensity and steady-state photoluminescence polarization assays. A preferred continuous source is a high-intensity, high-color temperature xenon arc lamp. The preferred source provides more light per unit time than flash sources, increasing sensitivity and reducing read times. A time-modulated source 102 provides light for time-resolved photoluminescence assays, such as photoluminescence lifetime and time-resolved photoluminescence polarization assays. A preferred time-modulated source is a xenon flash lamp. The preferred source produces a "flash" of light for a brief interval before signal detection and is especially well suited for time-domain measurements. Other time-modulated sources include pulsed lasers, as well as continuous lamps whose intensity can be modulated extrinsically using a Pockels cell, Kerr cell, or other mechanism. The latter sources are especially well suited for frequency-domain measurements. Analyzer 50 includes light source slots 103a–d for four light sources, although other numbers of light source slots and light sources also could be provided. The direction of light transmission through the photoluminescence optical system is indicated by arrows.

More generally, light sources include any sources of electromagnetic radiation of any wavelength capable of inducing photoluminescence or absorption in a composition. For example, light includes but is not limited to ultraviolet, visible, and infrared radiation. Suitable light sources include lamps, electroluminescence devices, lasers, light-emitting diodes (LEDs), and particle accelerators. Depending on the source and assay mode, light produced by such light sources may be 1) mono- or multichromatic, 2) polarized or unpolarized, 3) coherent or incoherent, and/or 4) continuous or time-modulated.

In analyzer 50, continuous source 100 and time-modulated source 102 produce multichromatic, unpolarized, and incoherent light. Continuous source 100 produces substantially continuous illumination, whereas time-modulated source 102 produces time-modulated illumination. Light fiom these light sources may be delivered to the sample without modification, or it may be filtered to alter its intensity, spectrum, polarization, or other properties.

Light produced by the light sources follows an excitation optical path to an examination site. Such light may pass through one or more "spectral filters," which generally comprise any mechanism for altering the spectrum of light that is delivered to the sample. Spectrum refers to the wavelength composition of light. A spectral filter may be used to convert white or multichlomatic light, which includes light of many colors, into red, blue, green, or other substantially monochromatic light, which includes light of one or only a few colors. In analyzer 50, spectrum is altered by excitation interference filters 104, which selectively transmit light of preselected wavelengths and selectively absorb light of other wavelengths. For convenience, excitation interference filters 104 may be mounted in an excitation filter wheel 106, which allows the spectrum of excitation light to be changed by rotating a preselected filter into the optical path. Spectral filters also may separate light spatially by wavelength, transmitting desired wavelengths by blocking or diverting undesired wavelengths. Examples include gratings, monochromators, and prisms.

Spectral filters are not required for monochromatic ("single color") light sources, such as certain lasers, which output light of only a single wavelength. Therefore, excitation filter wheel 106 may be mounted in the optical path of some light source slots 103a,b, but not other light source slots 103c,d.

Light next passes through an excitation optical shuttle 108, which positions an excitation fiber optic cable 110a,b in the light path to deliver light to top or bottom optics heads 112a,b, respectively. The optics heads include various optics for delivering light into the sensed volume and for receiving light transmitted from the sensed volume. Light is transmitted through a fiber optic cable much like water is transmitted through a garden hose. Fiber optic cables can be used easily to turn light around corners and to route light around opaque components of the analyzer. Moreover, fiber optic cables give the light a more uniform intensity profile. A preferred fiber optic cable is a fused silicon bundle, which has low autofluorescence. Despite these advantages, light also can be delivered to the optics heads using other mechanisms, such as mirrors.

Light arTiving at the optics head may pass through one or more excitation "polarization filters," which generally comprise any mechanism for altering the polarization of light. Polarization refers to the direction of the electric field associated with light. Excitation polarization filters may be included with the top and/or bottom optics head. In analyzer 50, polarization is altered by excitation polarizers 114, which are included only with top optics head 112a.

Light at one or both optics heads also may pass through an excitation "confocal optics element," which generally comprises any mechanism for focusing light into a "sensed volume." In analyzer 50, the confocal optics element includes an excitation aperture 116 placed in an image plane conjugate to the sensed volume, as shown in FIG. 5. The optical system projects an image of this aperture onto the sample, so that only a preselected or sensed volume of the sample is illuminated.

Light traveling through the optics heads is reflected and transmitted through a beamsplitter 118, which delivers reflected light to a composition 120 and transmitted light to a light monitor 122. The beamsplitter is changeable, so that it may be optimized for different assay modes or compositions. The light monitor is used to correct for fluctuations in the intensity of light provided by the light sources; such corrections are performed by reporting detected intensities as a ratio over corresponding times of the luminescence intensity measured by the detector to the excitation light intensity measured by the light monitor. The light monitor also can be programmed to alert the user if the light source fails. A preferred light monitor is a silicon photodiode with a quartz window for low autofluorescence.

The composition (or sample) is held in a sample container supported by a stage 123. The composition can include compounds, mixtures, surfaces, solutions, emulsions, suspensions, cell cultures, fermentation cultures, cells, tissues, secretions, and/or derivatives and/or extracts thereof. Analysis of the compositions may involve measuring the presence, concentration, or physical properties of a photoluminescent analyte in such a composition. The sample container can include microplates, gene chips, and or any array of samples in a known format. In analyzer 50, the preferred sample container is a microplate 124, which includes a plurality of microplate wells 126 for holding compositions. Composition may refer to the contents of a single microplate well, or several microplate wells, depending on the assay.

The position of the sensed volume within the composition created by the confocal optics element can be precisely moved to optimize the signal-to-noise and signal-to-background ratios. In analyzer 50, position in the X,Y-plane perpendicular to the optical path is controlled by moving the stage supporting the composition, whereas position along the Z-axis parallel to the optical path is controlled by moving the optics heads using a Z-axis adjustment mechanism 130, as shown in FIGS. 3 and 4. However, any mechanism for bringing the sensed volume into register or alignment with the appropriate portion of the composition also may be employed.

The combination of top and bottom optics permits assays to combine: (1) top illumination and top detection, or (2) top illumination and bottom detection, or (3) bottom illumination and top detection, or (4) bottom illumination and bottom detection. Same-side illumination and detection (1) and (4) is referred to as "epi" and is preferred for photoluminescence assays. Opposite-side illumination and detection (2) and (3) is referred to as "trans" and is prefelTed for absorbance assays. In analyzer 50, epi modes are supported, so the excitation and emission light travel the same path in the optics head. However, trans modes also could be supported and would be essential for absorbance assays. Generally, top optics can be used with any sample container having an open top, whereas bottom optics can be used only with sample containers having optically transparent bottoms, such as glass or thin plastic bottoms.

Light is transmitted by the composition in multiple directions. A portion of the transmitted light will follow an emission pathway to a detector. Transmitted light may pass through an emission aperture 131 and/or an emission polarizers 132. In analyzer 50, the emission aperture is placed in an image plane conjugate to the sensed volume and transmits light substantially exclusively from this sensed volume. In analyzer 50, the emission apertures in the top and bottom optical systems are the same size as the associated excitation apertures, although other sizes also may be used. The emission polarizers are included only with top optics head 112_a_. The emission aperture and emission polarizer are substantially similar to their excitation counterparts.

Transmitted light next passes through an emission fiber optic cable 134_a,b_ to an emission optical shuttle 136. This shuttle positions the appropriate emission fiber optic cable in front of the detection system. In analyzer 50, these components are substantially similar to their excitation counterparts, although other mechanisms also could be employed.

Light exiting the fiber optic cable next may pass through one or more emission "intensity filters," which generally comprise any mechanism for reducing the intensity of light. Intensity refers to the amount of light per unit area per unit time. In analyzer 50, intensity is altered by emission neutral density filters 138, which absorb light substantially independent of its wavelength, dissipating the absorbed energy as heat. These filters are changed by hand, although other methods also could be employed, such as a filter wheel. Intensity filters also may divert a portion of the light away from the sample without absorption. Examples include beam splitters, which transmit some light along one path and reflect other light along another path, and Pockels cells, which deflect light along different paths through diffraction.

Light next may pass through an emission interference filter 140, which may be housed in an emission filter wheel 142. In analyzer 50, these components are substantially similar to their excitation counterparts, although other mechanisms also could be employed. Emission spectral filters block stray excitation light, which may enter the emission path through various mechanisms, including reflection and scattering. If unblocked, such stray excitation light could be detected and misidentified as photoluminescence, decreasing the signal-to-background ratio. Emission interference filters can separate photoluminescence from excitation light because photoluminescence has longer wavelengths than the associated excitation light.

The relative positions of the spectral, intensity, polarization, and other filters presented in this description may be varied without departing from the spirit of the invention. For example, filters used here in only one optical path, such as intensity filters, also may be used in other optical paths. In addition, filters used here in only top or bottom optics, such as polarization filters, may also be used in the other of top or bottom optics or in both top and bottom optics. The optimal positions and combinations of filters for a particular experiment will depend on the assay mode and the composition, among other factors.

Light last passes to a detector, which is used in absorbance and hotoluminescence assays. In analyzer 50, there is one photoluminescence detector 144, which detects light from all photoluminescence modes. A preferred detector is a photomultiplier tube (PMT). Analyzer 50 includes detector slots 145_a–b_ for four detectors, although other numbers of detector slots and detectors also could be provided.

More generally, detectors comprise any mechanism capable of converting energy from detected light into signals that may be processed by the analyzer. Suitable detectors include photomultiplier tubes, photodiodes, avalanche photodiodes, and charge-coupled devices (CCDs). Depending on the detector and assay mode, such detectors may be used in (1) photon-counting or continuous modes, and (2) imaging or integrating modes.

Chemiluminescence optical system. FIGS. 3, 4, and 6 show the chemiluminescence optical system of analyzer 50. Because chemiluminescence follows a chemical event rather than the absolption of light, the chemiluminescence optical system does not require a light source or other excitation optical components. Instead, the chemiluminescence optical system requires only selected emission optical components. In analyzer 50, a separate chemiluminescence optical system is employed, which is optimized for maximum sensitivity in the detection of chemiluminescence.

Generally, components of the chemiluminescence optical system perform the same functions and are subject to the same caveats and alternatives as their counterparts in the photoluminescence optical system. The chemiluminescence optical system also can be used for other assay modes that do not require illumination, such as electrochemiluminescence.

The chemiluminescence optical path begins with a chemiluminescent composition 120 held in a sample container 126. The composition and sample container are analogous to those used in photoluminescence assays; however, analysis of the composition involves measuring the intensity of light generated by a chemiluminescence reaction within the composition rather than by light-induced photoluminescence. A familiar example of chemiluminescence is the glow of the firefly.

Chemiluminescence light typically is transmitted from the composition in all directions, although most will be absorbed or reflected by the walls of the sample container. A portion of the light transmitted through the top of the well is collected using a chemiluminescence head 150, as shown in FIG. 3, and will follow a chemiluminescence optical pathway to a detector. The direction of light transmission through the chemiluminescence optical system is indicated by arrows.

The chemiluminescence head also includes a mechanism for transmitting light from a sensed volume within the composition. Detecting from a sensed volume reduces contributions to the chemiluminescence signal resulting from "cross talk," which is pickup from neighboring wells. The confocal optics element includes a chemiluminescence baffle 152, which includes rugosities 153 that absorb or reflect light from other wells. The confocal optics element also includes a chemiluminescence aperture 154 that further confines detection to a sensed volume.

Light next passes through a chemiluminescence fiber optic cable 156. This fiber optic cable is analogous to excitation and emission fiber optic cables 110a,b and 134a,b in the photoluminescence optical system.

Light next passes through one or more chemiluininescence intensity filters, which generally comprise any mechanism for reducing the intensity of light. In analyzer 50, intensity is altered by chemiluminescence neutral density filters 158.

Light last passes to a detector, which conveits light into signals that may be processed by the analyzer. In analyzer 50, there is one chemiluminescence detector 160. A preferred detector is a photomultiplier tube. This detector has optimal sensitivity to blue/green light of the type most often produced in chemiluminescence.

Optics Heads and the Generation of Sensed Volumes

Figure 7:
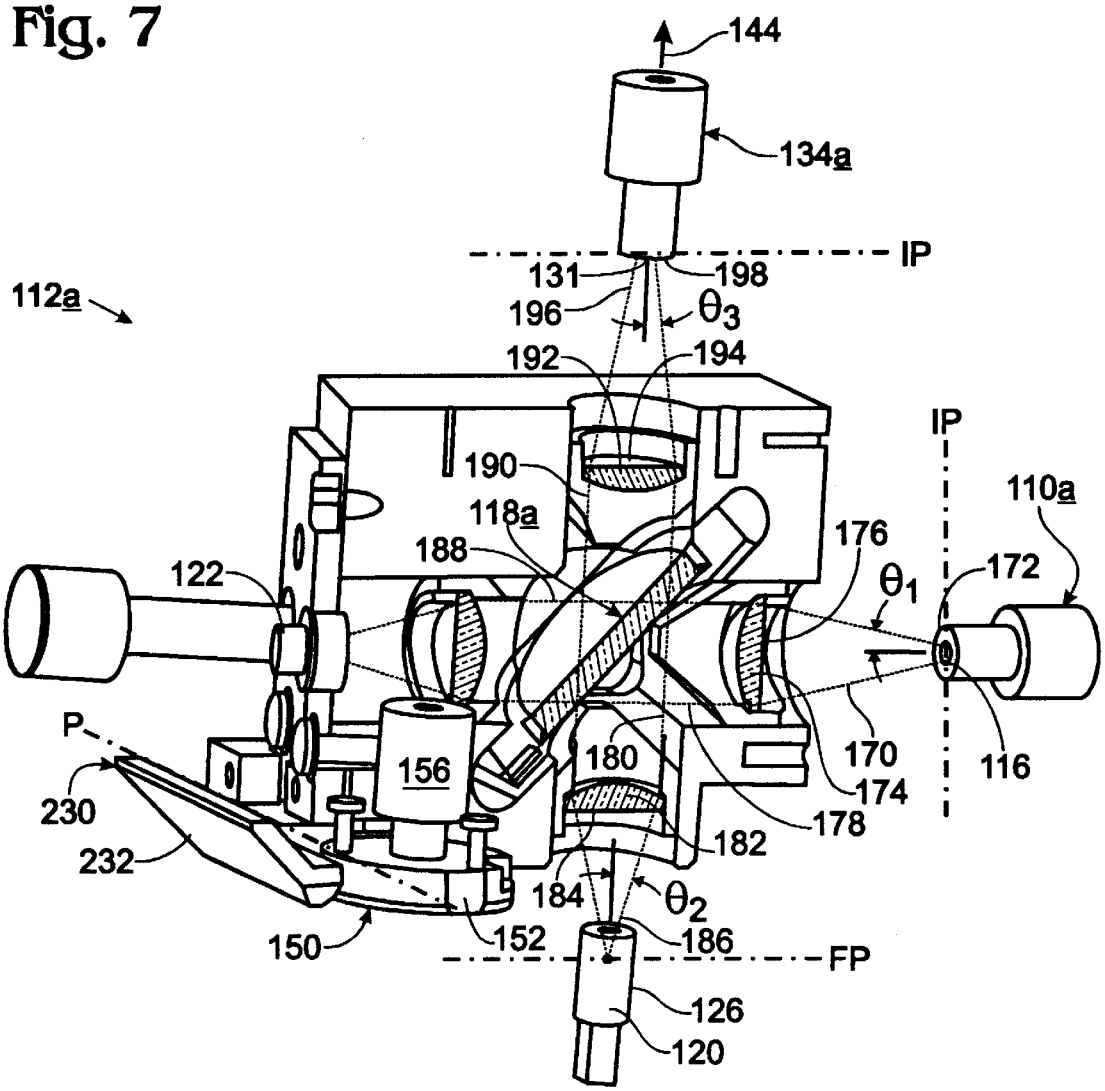
FIG. 7 is a cross-sectional view of an optics head employed in an embodiment of the invention.
Figure 8:
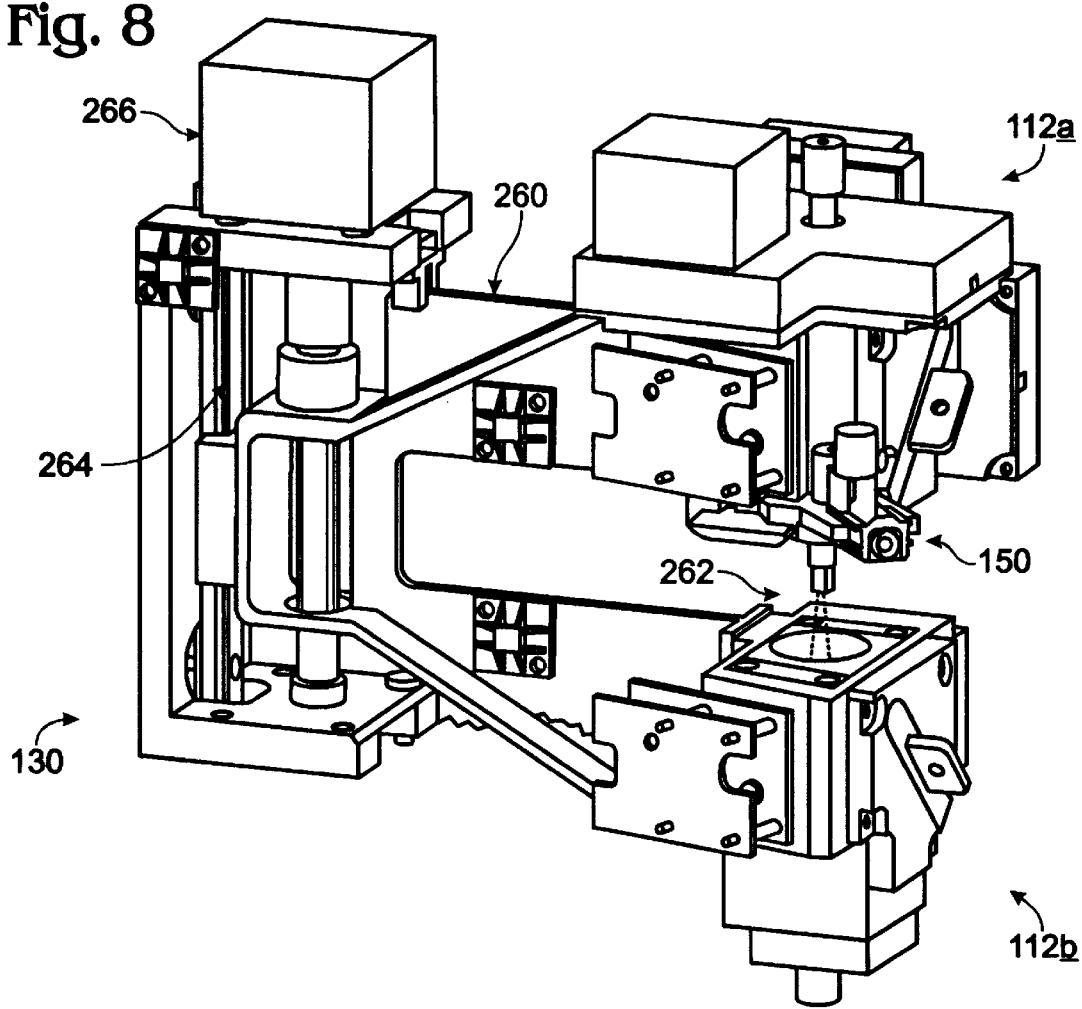
FIG. 8 is a partial perspective view of top and bottom optics heads that are used in a preferred embodiment of the invention.

FIG. 7 shows top optics head 112a, which is used together with fiber optic cables 110a, 134a and apertures 116, 131, as shown in FIG. 5, to create the sensed volume. Top optics head 112a is substantially similar to bottom optics head 112b, as shown in FIG. 8, except that the top optics head includes chemiluminescence head 150 and excitation and emission polarizers 114, 132 (not shown).

Excitation light aitives at top optics head 112a, through excitation fiber optic cable 110a. Fiber optic cables are cylindrical waveguides that transmit light through a process known as total internal reflection. Fiber optic cables are characterized by a numerical aperture, which describes the largest angle an incident ray can have for total internal reflection in the cable. Specifically, the numerical aperture is defined as $$NA = n \sin \theta$$

where NA is the numerical aperture, n is the index of refraction of the medium adjacent the fiber optic cable, and $\theta$ is the half angle of the cone of incident light. Here, the medium adjacent the fiber optic cable is air, so n=1. The higher the numerical aperture, the greater the angle over which the fiber optic cable can collect and transmit light.

Excitation light exits the fiber optic cable through excitation aperture 116 at a cone angle $\theta_1$ deteimined in pail by the numerical aperture of the fiber optic cable. In analyzer 50, this light resembles a cone 170, with its apex positioned just inside the tip 172 of fiber optic cable 110a. In analyzer 50, excitation light first may pass through an excitation polarizer 114 (not shown). Excitation light next passes through a first plano-convex converging lens 174, whose plan side 176 is oriented toward the fiber optic cable. This lens is positioned so that it substantially converts cone 170 of excitation light into a cylinder 178 of excitation light. This conversion is accomplished by positioning tip 172 substantially at the focal point of first lens 174.

Excitation light next impinges on beamsplitter 118a. Beamsplitter 118a reflects a portion 180 of the incident light toward composition 120 in sample well 126. Light portion 180 then impinges on a second plano-convex converging lens 182, whose plan side 184 is oriented away from beamsplitter 118a. Lens 182 converts cylindrical light portion 180 of excitation light back into a cone 186 of excitation light, which is focused onto and thus delivered to composition 120 in sample well 126. The cone angle $\theta_2$ of cone 186 is determined in part by the numerical aperture of second lens 182, and may be different from that of the excitation light exiting the fiber optic cable.

Beamsplitter 118a also transmits a portion 188 of the incident light to light monitor 122, which functions as described above. The optics used to focus the transmitted light into the light monitor may be substantially similar to the optics used to focus the reflected light into the sample well. Alternatively, the optics may be a lensless system, such as a black tapered cone to direct light.

The excitation light may induce photoluminescence within the composition. Photoluminescence light has longer wavelengths than the associated excitation light. This is due to conservation of energy; in photoluminescence, a portion of the excitation energy is lost as heat, so that no more than the remaining portion of the excitation energy can be re-emitted as lower-energy (i.e., longer-wavelength) light.

A conical portion of the photoluminescence substantially coextensive with the cone 186 of excitation light can pass back through second lens 182, which converts the cone of emission light into a cylinder of emission light substantially coextensive with cylindrical light portion 180 of excitation light.

Emission light next impinges on beamsplitteri 118a, which transmits a portion toward photoluminescence detector 144. Beamsplitter 118a typically is chosen for two scenarios. If a large number or variety of luminescent molecules are to be studied, a "50:50" beamsplitter that reflects half and transmits half of the incident light is optimal. Such a 50:50 distribution is the best compromise between reflecting or delivering the most excitation light onto the composition and transmitting the most emission light to the detector. If one or a few related luminescent molecules are to be studied, a "dichroic" or "multichroic" beamsplitter is optimal. Such a beamsplitter can reflect most or substantially all of the excitation light, while transmitting most or substantially all of the emission light. This is possible because the reflectivity and transmissivity of the bearnsplitter can be varied with wavelength.

Emission light 190 transmitted through beamsplitter 118a impinges on a third plano-convex converging lens 192, whose plan side 194 is oriented away from the beamsplitter. In analyzer 50, emission light first may pass through an emission polarizer 132, as shown in FIG. 5. Third lens 192 focuses the cylinder of light 190 into a cone of light 196 that impinges on emission fiber optic cable 134a for transmission to photoluminescence detector 144. To be transmitted by the fiber, the light should be focused onto emission aperture 131 at the tip 198 of the fiber as a spot comparable in size to the diameter of the fiber optic cable. Moreover, the incident cone angle $\theta_3$ should not exceed the inverse sine of the numerical aperture of the fiber.

A property of the optical arrangement in top optics head 112a is that the tips 172, 198 of fiber optic cables 110a, 134a and the sensed volume of the composition are "confocal." Confocal means that all three objects are in conjugate focal planes, so that whenever one is in focus, all are in focus. The sensed volume of the composition lies in a focal or sample plane FP of the system, and the tips of the fiber optic cables lie in image planes IP of the system. The detector also may be placed in an image plane, so that it detects the composition in focus. The tips of the fiber optic cables may be said to lie in intermediate image planes, because light may pass through these planes, and the detector may be said to lie in a terminal image plane, because light terminates on the detector.

The sensed volume is created by placing confocal optics elements in or near one or more intermediate image planes. A preferred confocal optics element is an aperture. If such an aperture is placed in the excitation optical path, an image of the aperture will be focused onto the composition. As a result, only a portion of the composition within the focal plane corresponding to the shape and proportional to the size of the aperture will be illuminated, and only luminescent molecules in or near that portion of the focal plane will be induced to emit photoluminescence. If such an aperture is placed in the emission optical path, an image of the aperture will be focused onto the detector. Luminescence that would ordinarily focus onto a part of the detector outside the image of the aperture will be blocked or masked from reaching the detector.

The shape of the sensed volume depends on the confocal optics elements, such as excitation and emission apertures 116, 131, the light source, and the numerical apertures of the lenses and fiber optic cables. Generally, the intensity of the sensed volume will be greatest at the center of the sensed volume, and will decay monotonically in all directions away from the center. Most of the intensity will lie within a distance equal to about one aperture diameter from the center of the sensed volume in the Z direction, and within about one-half an aperture diameter fiom the center of the sensed volume in the X and Y directions.

FIG. 7 also shows a sample container sensor switch 230, which is used to prevent damage to optics head 112a by preventing the optics head from physically contacting a sample container. Sample container sensor switch 230 is mounted about a pivot axis P adjacent chemiluminescence head 150. Sample container sensor switch 230 includes a sensor surface 232 positioned so that a sample container must contact the sensor surface before contacting any component of top optics head 112a. Contact between a sample container and sensor surface 232 causes sample container sensor switch 230 to pivot about pivot axis P, which activates an electrical circuit that turns off power to the mechanism(s) used to move the sample container.

A sample container sensor switch is especially important in an analyzer designed for use with a variety of sample containers, because it reduces the likelihood of damage both from exotic sample holders with unusual dimensions and from standard sample holders with aberrant or misidentified dimensions. The sample container sensor switch may detect impending contact between the sample container and optics head (1) mechanically, as in the preferred embodiment, (2) optically, as with an electric eye, (3) acoustically, as with an ultrasonic detector, or (4) by other mechanisms.

FIG. 7 also shows chemiluminescence head 150, which includes chemiluminescence baffle 152 and chemiluminescence fiber optic cable 156. Chemiluminescence head 150 is mounted on top optics head 112a, but also could be mounted on bottom optics head 112b or on both top and bottom optics heads 112a,b.

Figure 7A:
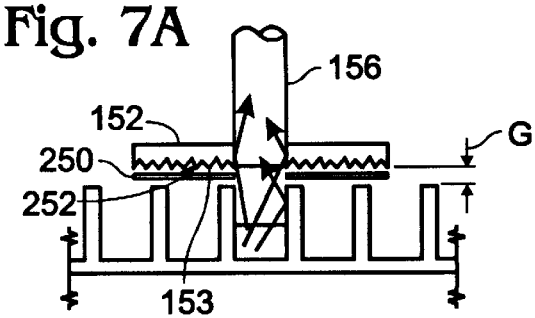
FIG. 7A is a cross-sectional view of a chemiluminescence head employed in an embodiment of the invention.

FIG. 7A shows an alternative view of cheiniluminescence head 150. In chemiluminescence, emission light sensitivity is maximized by detecting as much emission light as possible from the top of the sample container. In analyzer 50, this is accomplished by placing fiber optic cable 156 directly above and aligned with the center of the microplate well or other sample container. Fiber optic cable 156 has an "effective" diameter substantially equal to the diameter of the microplate well and a numerical aperture sufficient to collect most or substantially all of the light emitted from the composition. The effective diameter of fiber optic cable 156 may be adjusted to match the size of the microplate well using a sliding aperture plate, which is placed at the end of the fiber optic cable. For example, sliding aperture plate may include separate apertures for 96, 384, 768, 1536, 3456, and 9600 well plates, where each aperture is optimized for the well size associated with each microplate.

Light detection further is enhanced by positioning fiber optic cable 156 so that the gap G or flying height between fiber optic cable and the top of the sample is as small as possible. Generally, if the gap between the top of the microplate and the fiber optic cable is small compared to the diameter of the fiber optic cable, most of the emission light will be collected. In analyzer 50, preferred values of G lie in the range 0.25–1.5 mm, depending on the type of microplate. The preferred values allow for normal variations in microplate thickness and minimize the possibility of contacting liquid that may be on the surface of the microplate. This is accomplished by accurate calibration of the travel of the optical head along the Z-axis relative to a reference point on the Z-axis. The height of various microplates can be stored in software so that G can be set by the instrument to a pre-selected value.

Gap G also can be determined empirically using a precision top-of-plate sensor, which is mounted on the bottom of the upper optics head. The height of the plate is measured by slowly moving the optics head toward the plate until the top-of-plate sensor indicates that a known flying height has been achieved. With this approach, the height of the plate need not be known in advance. Moreover, if a microplate mistakenly is inserted into the machine with a greater than expected height, the top-of-plate sensor can be used to prevent the optics head from colliding with the microplate.

Chemiluminescence head 150 also includes a chemiluminescence baffle 152, which supports fiber optic cable 156, and aperture support slide 250, which minimizes detection of chemilurninescence from neighboring wells. Detection from neighboring wells may be referred to as "cross talk." In analyzer 50, chemiluminescence baffle 152 is generally circular and includes a black surface 252 with rugosities 153 designed to absorb light. Chemiluminescence baffle 152 allows low cross talk to be achieved at comfortable flying heights.

Alternative embodiments of the chemiluminescence optical system could include a plurality of chemiluminescence heads optically connected to a plurality of chemiluminescence detectors. The chemiluminescence heads could be mounted as a linear array or as a matrix. For example, a linear array of 8 or 12 chemiluminescence heads optically connected to 8 or 12 detectors could be used to detect simultaneously from entire rows or columns of a 96-well microplate. Moreover, the same arrays also could be used with the appropriate apeitures to detect from higher-density plates in which the well-to-well spacing is evenly divisible into the well-to-well spacing in the 96-well plate, as for 384 and 1536-well plates. The chemiluminescence heads also could be mounted as a matrix that could detect from one or more plate formats.

Other alternative embodiments of the chemiluminescence optical system could include a plurality of fiber optic cables connected as a bundle to a CCD detector or to a PMT array. The fiber optic bundle could be constructed of discrete fibers or of many small fibers fused together to form a solid bundle. Such solid bundles are commercially available and easily interfaced to CCD detectors.

These alternative embodiments may be used with alternative embodiments of chemiluminescence baffle 152. For example, with a fiber optic bundle, cross-talk between wells within the matrix can be minimized by keeping G as small as possible and/or by applying an anti-reflective coating to the face of the fiber bundle. An anti-reflective coating can reduce reflected light from about 4% to less than 1%. In addition, a baffle having a rough black surface as described above could be placed around the outside of the fiber bundle, like a collar, to minimize pick-up from areas of the plate that are not under the bundle.

FIG. 8 shows the relationship between top and bottom optics heads 112a,b and chemiluminescence head 150. Top and bottom optics heads 112a,b are coupled to a common optics head support structure 260, which includes a gap 262 through which a stage and sample container can pass. Optics head support structure 260 is configured so that top and bottom optics heads 112a,b are fixed relative to one another and positioned so that excitation light transmitted by one head can be detected by the other head. This arrangement facilitates absorbance assays.

FIG. 8 also shows a Z-axis adjustment mechanism 130, which is used to adjust the position of the sensed volume within a composition. This adjustment is performed by adjusting the positions of top and bottom optics heads 112a,b relative to a sample container positioned in gap 262. Z-axis adjustment mechanism 130 includes a support track 264 substantially parallel to a Z-axis on which optics head support structure 260 is mounted. Z-axis adjustment mechanism 130 also includes a motor 266 for moving optics head support structure 260 along support track 264. Relative movement of the optics heads and sample container is effected by moving the optics heads while keeping the sample container stationary, although other mechanisms also can be employed, such as moving the sample container while keeping the optics heads stationary.

Application of Sensed Volumes

The optical system described above, and the confocal optics elements in particular, allow detection of luminescence substantially exclusively from a sensed volume of a composition.

Figure 9:
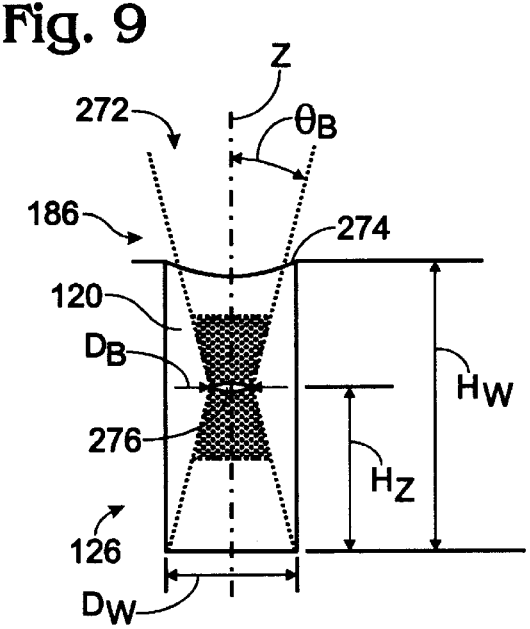
FIGS. 9–12 are schematic views of sensed volumes in microplate wells.

FIG. 9 shows a standard microplate well 126 and an excitation light beam 186 as it illuminates the well. The standard well is cylindrical and may be characterized by a diameter $D_W$ and a height $H_W$. Other wells may have other geometries and be characterized by other quantities; for example, a well could be square and characterized by a width and a height, or a well could be conical and characterized by a cone angle and a height. The interface between composition 120 and the air 272 is termed the meniscus 274 and may be convex, plan, or concave.

Excitation light beam 186 is focused by the optical system so that it is shaped much like an hourglass along the optical (Z) axis. This hourglass shape arises as the cone of excitation light formed by the optics passes through focus. The diameter $D_B$ of the beam is smallest at the beam's waist 276, which corresponds to the focal plane, above and below which the beam diverges monotonically, making an angle $\theta_B$ with respect to the vertical or Z-axis. Values of $D_B$ and $\theta_B$ depend on optical components of the analyzer and may be varied by changing these components. Generally, $D_B$ and $\theta_B$ are inversely related. The distance between the bottom of the well and the beam waist is termed the focal (Z) height, $H_z$.

The shape of the sensed volume, indicated by stippling, may differ in directions parallel and perpendicular to the optical or Z-axis. Parallel to the Z-axis, the shape may be Lorentzian, among others. Perpendicular to the Z-axis, the shape may be Gaussian, or it may be a rounded pulse function, among others. A laser beam might give rise to a Gaussian, whereas a fiber optic bundle might give rise to a rounded pulse fuiction. Generally, lower numerical apertures will create sensed volumes shaped more like cylinders, whereas higher numerical apertures will create sensed volumes shaped more like hourglasses.

The shape and volume of the sensed volume may be adapted like a probe to match the shape and volume of the sample container. Thus, the sensed volume may be expanded for maximum signal in a large sample container, and contracted to avoid nearby walls in a small sample container. The shape and volume of the sample container also may be chosen or designed to confoim to the shape and volume of the sensed volume.

Alternatively, the sensed volume may be held constant. In this way, the sensed volume will report on equal volumes of each composition analyzed, so that the analyzer effectively reports "intensive" quantities. Intensive quantities do not depend on the amount of composition in a sample container; in contrast, extensive quantities do depend on the amount of composition in the sample container. This approach can be used to facilitate comparison of results obtained from sample containers with different-sized sample wells, such as 96 and 384 well microplates. In addition, it can be used to reduce artifacts reflecting fluctuations in sample volume in sample containers with same-sized sample wells.

Figure 10:
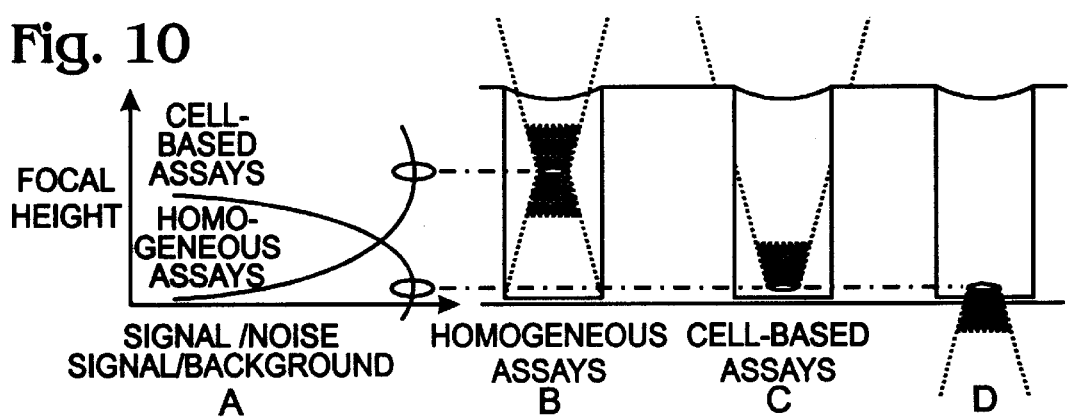

FIG. 10 shows how the signal-to-noise and signal-to-background ratios are affected by focal height for two assay modes. In homogeneous assays (Panel B), photoluminescent molecules are distributed uniformly throughout the composition, and the optimum signal-to-noise and signal-to-background ratios are obtained regardless of well geometry when the sensed volume is positioned in the middle of the composition (Panel A), so that the sensed volume does not overlap with the meniscus or the bottom or sides of the well. If the meniscus is in the sensed volume, light reflected from the meniscus will be detected. This will decrease sensitivity by increasing background and decreasing signal. If the bottom of the well is in the sensed volume, light reflected from the well bottom will be detected. Moreover, noncomposition photoluminescence arising from fluorescent and other photoluminescent materials that are commonly included in the microplate or adsorbed to the walls of the microplate also will be detected. These two effects will decrease sensitivity by increasing background and decreasing signal. Luminescence measured from the microplate walls will lead to spuriously high lumin escence intensitie s and luminescence p olarizations.

In cell-based assays (Panels C and D), photoluminescent molecules are concentrated in or near cells growing at the bottom of the well, and the optimum signal-to-noise and signal-to-background ratios are obtained when the sensed-volume is centered about the bottom of the well (Panel A). Such centering may be accomplished either using top optics (Panel C) or bottom optics (Panel D). This conclusion will hold for any two-dimensional or quasi-two-dimensional composition, where the third dimension is smaller than the sensed volume.

The shape and position of the sensed volume within the well are affected by (1) the meniscus, (2) the geometry of the microplate well, and (3) the geometry of the whole microplate.

Figure 11:
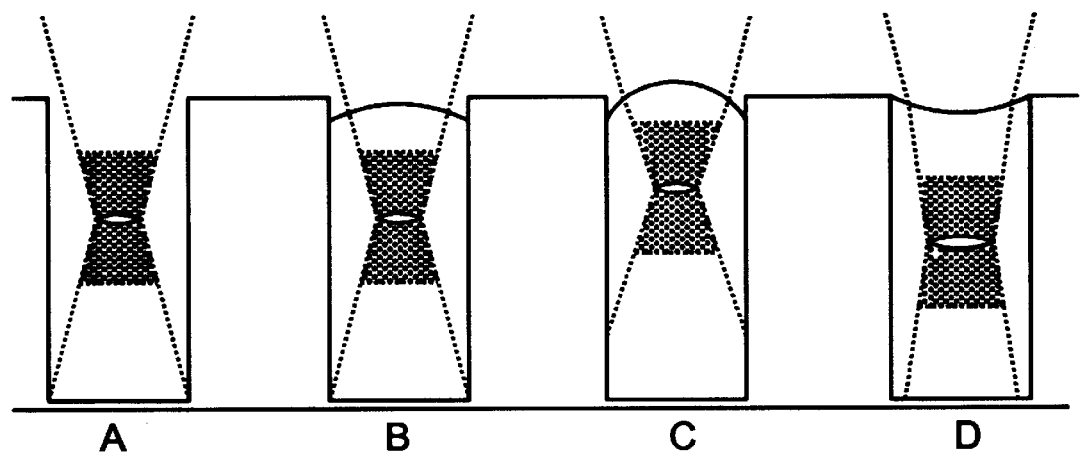

FIG. 11 shows how the meniscus affects the shape and position of the sensed volume. When there is no fluid and hence no meniscus, the beam has a nominal shape; see Panel A. The meniscus affects the sensed volume because light is refracted as it crosses the meniscus boundary between the air and the composition. Specifically, light passing from air (with its lower index of refraction) to the composition (with its higher index of refraction) bends toward the normal, as described by Snell's law. Here, the normal is the direction perpendicular to the surface of the meniscus at a given point. If the meniscus is everywhere perpendicular to the light beam, then light passing through the meniscus will not bend, and the beam will retain its nominal undistorted shape. For a converging beam, this will occur when the meniscus is appropriately convex; see Panel B. If the meniscus is more than appropriately convex, light will bend toward the middle of the well as it passes through the meniscus, and the sensed volume will be compressed and raised; see Panel C. If the meniscus is less than appropriately convex, flat, or concave, light will bend away from the middle of the well as it passes through the meniscus, and the sensed volume will be stretched and lowered; see Panel D. Meniscus effects could be minimized by appropriately configuring microplate wells.

Figure 12:
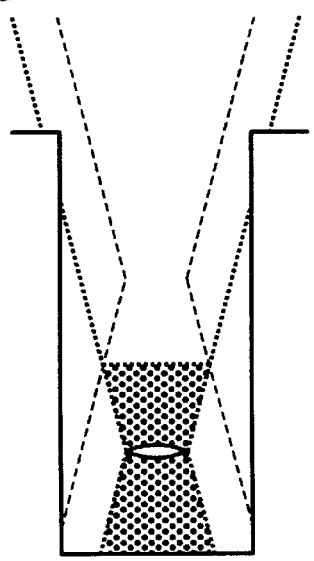
Figure 13:
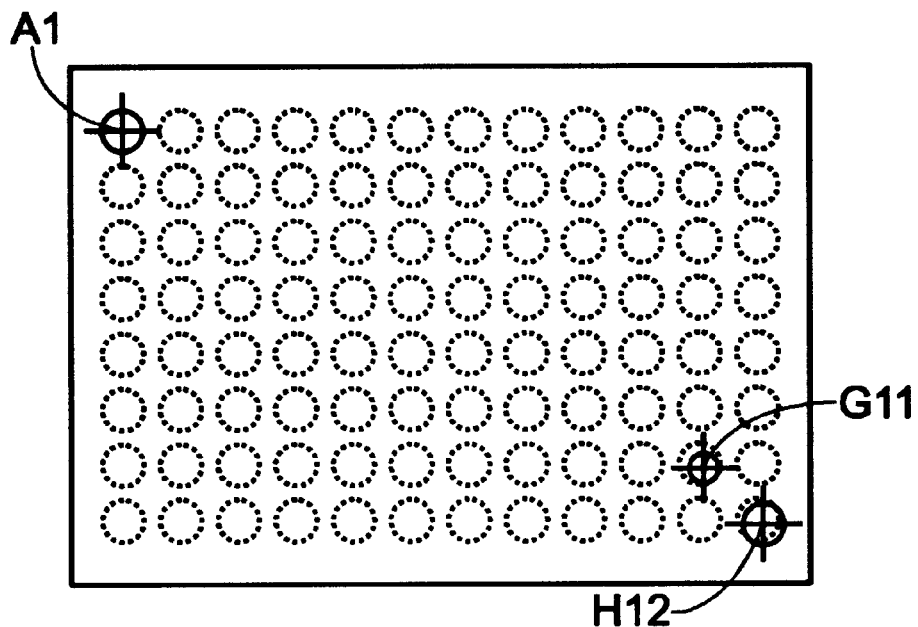
FIG. 13 is a schematic top view of a microplate.

FIGS. 12 and 13 show how the geometry of the microplate well affects the position of the sensed volume. In particular, if the well is sufficiently narrow relative to the diameter of the beam or if the well is sufficiently deep relative to the angle made by the beam, then the light beam may impinge upon the top walls of the well. Setting the Z-height too low can reduce sensitivity (1) by decreasing the desired signal because less light enters the well, and (2) by increasing the background because the light beam illuminates the tops of wells. Many microplates are made from materials that are fluorescent or otherwise photoluminescent, and the instrument will detect this photoluminescence from materials at the tops of wells.

FIG. 13 shows how the geometry of the microplate affects the position of the sensed volume. The analyzer is configured automatically to find the location of each well in a given microplate, beginning with well A1. The analyzer does this using stored parameters describing the dimensions (plate heights, interwell distances, etc.) of the particular microplate style. However, these microplate parameters are nominal values and do not account for unit-to-unit or lot-to-lot variations in microplate geometry. If there is a slight variation in interwell distance, the light beam can be off-center on some wells even though it is perfectly centered on well A1. This effect is termed cross-plate drift.

Cross-plate drift of fluorescence readings may increase as the instrument scans across the microplate as variations are compounded. Typically, drift will be worst at well H12, which is farthest from well A1. Such drift can be reduced by making the stage more accurate, by making the sample containers of a more consistent size, or by increasing $H_z$, which will reduce the diameter of the beam and put it back into the well. The lattermost approach is shown for well G11.

Figure 14:
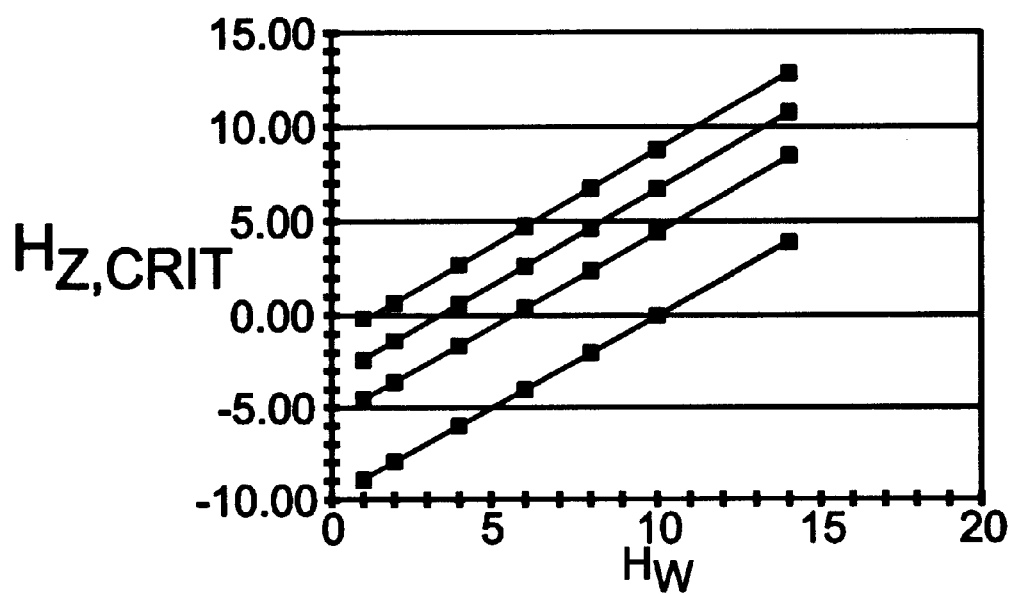
FIG. 14 is a graph showing the relationships between critical Z-height and microplate well height.

Because beam position is a critical determinant of signal to noise, Z height must be appropriately maintained; Z height should be kept above a critical focal height, $H_{Z,Crit}$. The height at which the beam first impinges on the walls of the well is the critical focal height, $H_{Z,Crit}$. FIG. 14 shows how $H_{Z,Crit}$ depends on the well height $H_W$ and well diameter $D_W$, for a beam of diameter 1.5 millimeters (mm) and a beam angle $\theta_B$ of 12.7 degrees. Similarly, Table 1 shows how $H_{z,crit}$ depends on well height and well diameter for four commercially available microplates.

| Plate Type | Well Height (mm) | Well Diameter (mm) | $H_Z$, Crit (mm) |
| --- | --- | --- | --- |
| Costar Black Flat Bottom 96-Well 3915 | 10.71 | 6.71 | −0.85 |
| Dynatech MicroFluor Round Bottom | 9.99 | 6.78 | −1.72 |
| Costar Black 384-Well 3710 | 11.55 | 3.66 | 6.76 |
| Packard White 384-Well #6005214 | 11.57 | 3.71 | 6.67 |

Z-height can be optimized for a particular microplate and chemistry by (1) preparing a test microplate with representative chemistry (e.g., blanks, positive and negative controls, dilution series), (2) and reading the microplate multiple times at different Z-heights to determine the Z-height that gives the best signal-to-background data. Some combinations of chemistry and microplate are relatively insensitive to Z-height, while others demonstrate a distinct optimum.

As described above, a sample container sensor switch is mounted on the top optics head to prevent the plate from contacting the optics head in case the plate is misaligned, not properly specified, or the Z-height is set incorrectly. If this sensor detects a fault, the sample container will be ejected prior to reading.

Although this discussion was presented for the preferred sample container, microplates, the same principles will apply with other sample containers.

Light Source and Detector Modules

Figure 15:
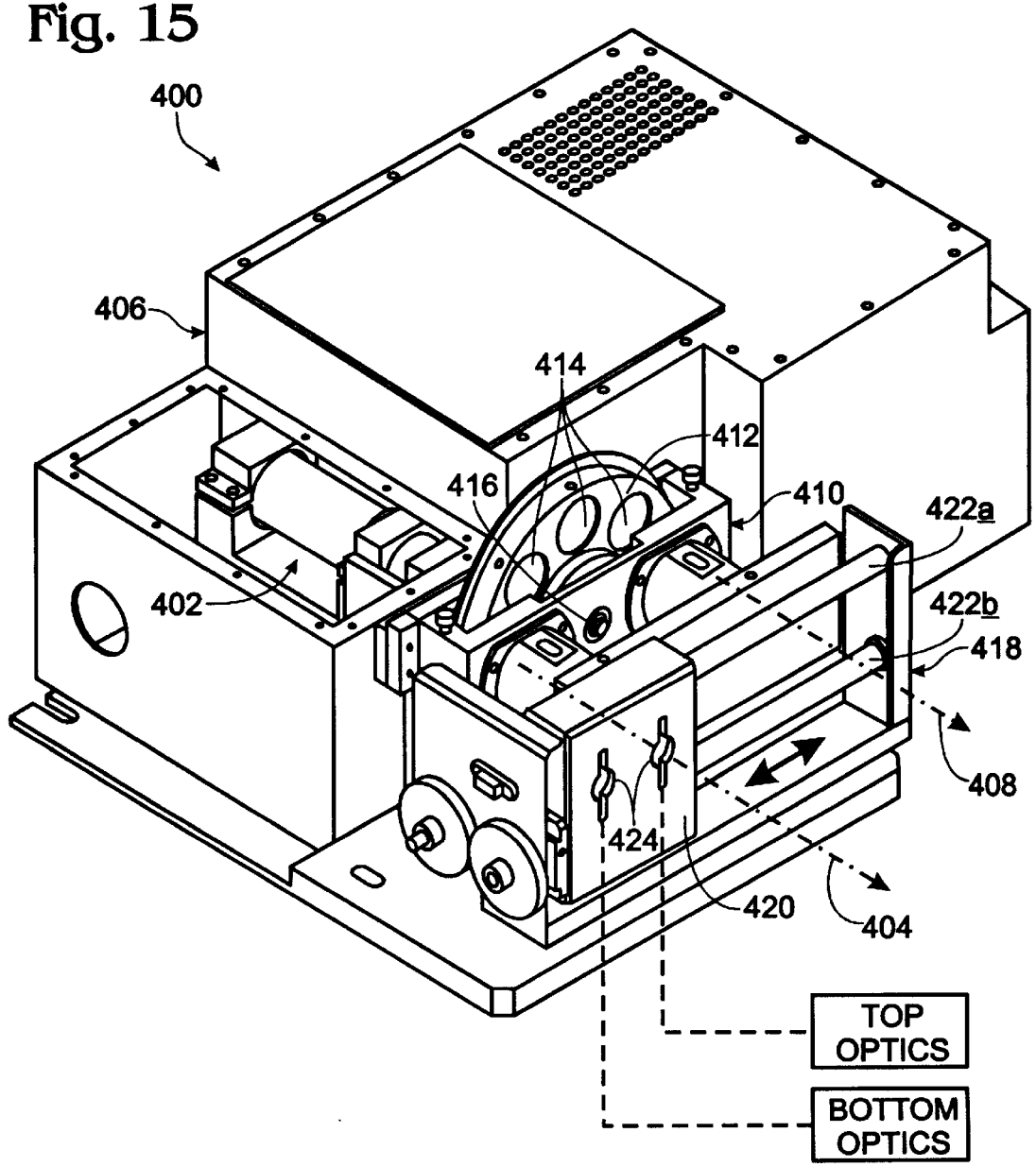
FIG. 15 is a partial perspective, paitial schematic view of a light source module employed in a preferred embodiment of the present invention.

FIG. 15 is a perspective view of a light source module employed in a preferred embodiment of the invention. Portions of the module case have been removed to reveal internal componentry. Light from flashlamp 402 travels along light path 404. A second light source, namely, a continuous arc lamp (not shown) is provided in compartment 406. The arc lamp directs light along light path 408. Filter wheel assembly 410 is positioned adjacent the light source compartments. Filter wheel assembly 410 includes filter wheel 412 which holds a plurality of filters 414. Filter wheel 412 is rotatable around axis 416 so that a given filter can be positioned interchangeably along light path 404, or along light path 408, by rotating filter wheel 412. Fiber optic shuttle assembly 418 is mounted next to filter wheel assembly 410. Movable shuttle 420 translates along support tracks 422a and 422b, so that shuttle 420 can be positioned in front of a selected light source for a particular assay application. Two fiber optic ports 424 are provided on an external face of shuttle 420. Fiber optic ports 424 direct light, via fiber optic cables, from a selected source to either the top optics head or the bottom optics head, above and below the stage, respectively.

As shown in FIG. 16, light detector module 440 is similar to light source module 400 in many respects. Light detector 442 receives light directed along light path 444, originating from a composition at the examination site near the stage. Filter wheel assembly 446 is positioned in front of detector 442. Filter wheel 448 includes a plurality of filters 450 that rotate around axis 451. A second detector poit 452 is provided in filter wheel assembly 446 so that a second detector can be mounted in the light detector module. A given filter in filter wheel 448 can be positioned along light path 444 leading to detector 442, or alternatively can be positioned along a light path leading to the second detector (not shown). A polarizer mechanism 454 is mounted adjacent to filter wheel assembly 446. Fiber optic shuttle assembly 456 is mounted in front of polarizer mechanism 454. Shuttle assembly 456 includes shuttle 458 which is movable along upper and lower support tracks 460a and 460b, respectively. An exterior face of shuttle 458 has two fiber optic ports 462, one of which is connected, via a fiber optic cable, to the top optics head above the examination site, while the other port is connected, via a fiber optic cable, to the bottom optics head below the examination site. In operation, shuttle 458 can be moved along support tracks 460a and 460b in order to optically connect either one of the optics heads to any one of the detectors (if more than one is included in the module), and through any one of filters 450 in filter wheel 448.

Comparison of FIGS. 15 and 16 shows that many aspects of light source module 400 and detector module 440 are the same, particularly the mechanics of filter wheel assemblies 410 and 446, and fiber optic shuttle assemblies 418 and 456. Collectively, the light source and detector modules provide a great deal of analytical flexibility to select different combinations of light sources, detectors, and filters for different applications, while also being able to select different combinations of top versus bottom illumination and detection orientations.

FIGS. 17–21 illustrate floating head assembly embodiments that are employed inside a fiber optic shuttle assembly for the purpose of creating and maintaining light-tight connections between selected light sources or detectors and fiber optic cables that lead to the examination site. FIG. 17 is a partial perspective view of fiber optic shuttle assembly 480. Shuttle 481 contains two floating head assemblies 482, each of which is connected to a fiber optic cable that leads to either the top optics head or the bottom optics head, above and below the stage, respectively.

FIG. 18 show a perspective view of one of floating head assemblies 482. Fiber optic ferrule 484 is contained inside floating head assembly 482 for transmitting light. Fiber optic ferrule 484 is encompassed by movable seal 486 which extends beyond the top of fiber optic ferrule 484. Outer case 488 contains the inner elements of floating head assembly 482. FIG. 19 is a cross-sectional view of floating head assembly 482. Movable seal 486 is forced upward by spring 490. Flange 492 on movable seal 486 contacts retaining ring 494 when seal 486 is maximally extended. As shown in FIG. 19, floating head assembly 482 is positioned such that fiber optic ferrule 484 is aligned with light transmission port 496 in plate 498. Seal 486 automatically accommodates or floats relative to a lower suiface 499 of plate 498 so that a light-tiglht seal is maintained.

Figure 20:
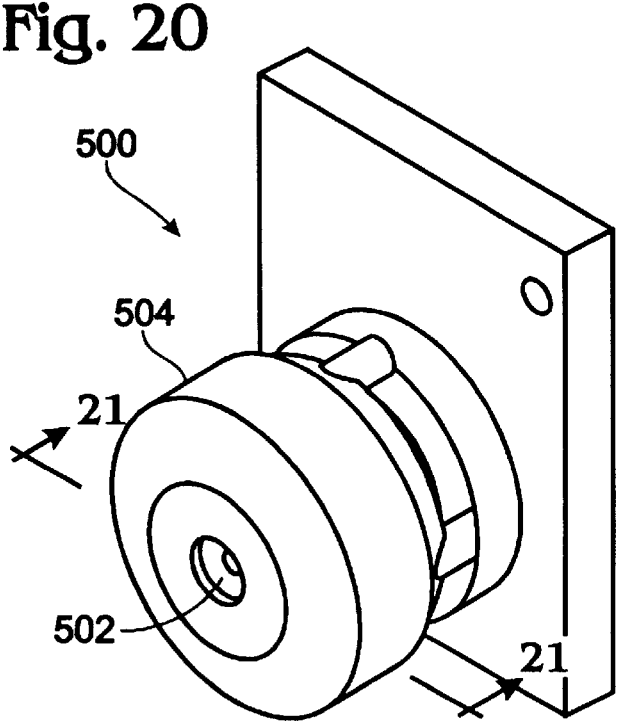
FIG. 20 is a perspective view of an alternate floating head assembly.
Figure 21:
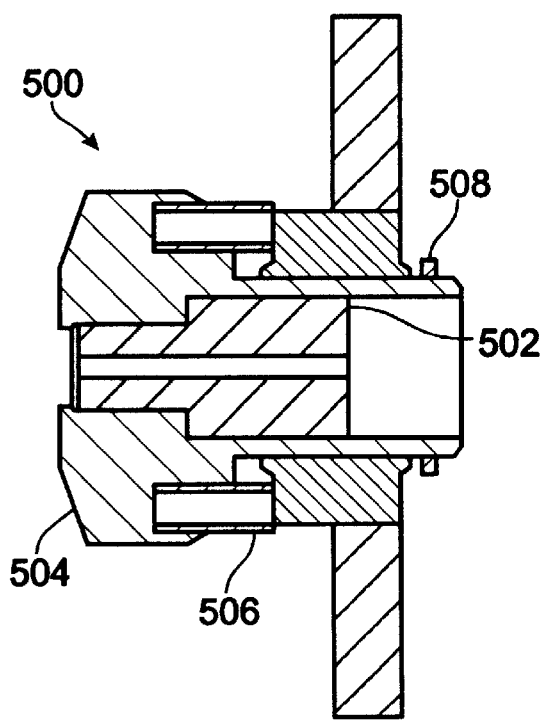
FIG. 21 is a cross-sectional view of the floating head assembly shown in FIG. 20.

FIGS. 20 and 21 illustrate an alternative floating head assembly embodiment. FIG. 20 show a perspective view of floating head assembly 500 internal fiber optic ferrule 502 is capped by movable seal 504. A cross-sectional view of floating head assembly 500 is show in FIG. 21. Spring 506 forces movable seal 504 forward into contact with a plate (not shown) that defines light transmission ports in a fiber optic shuttle assembly, as previously described. Retaining ring 508 prevents over-extension of movable seal 504.

Stage

Figure 22A:
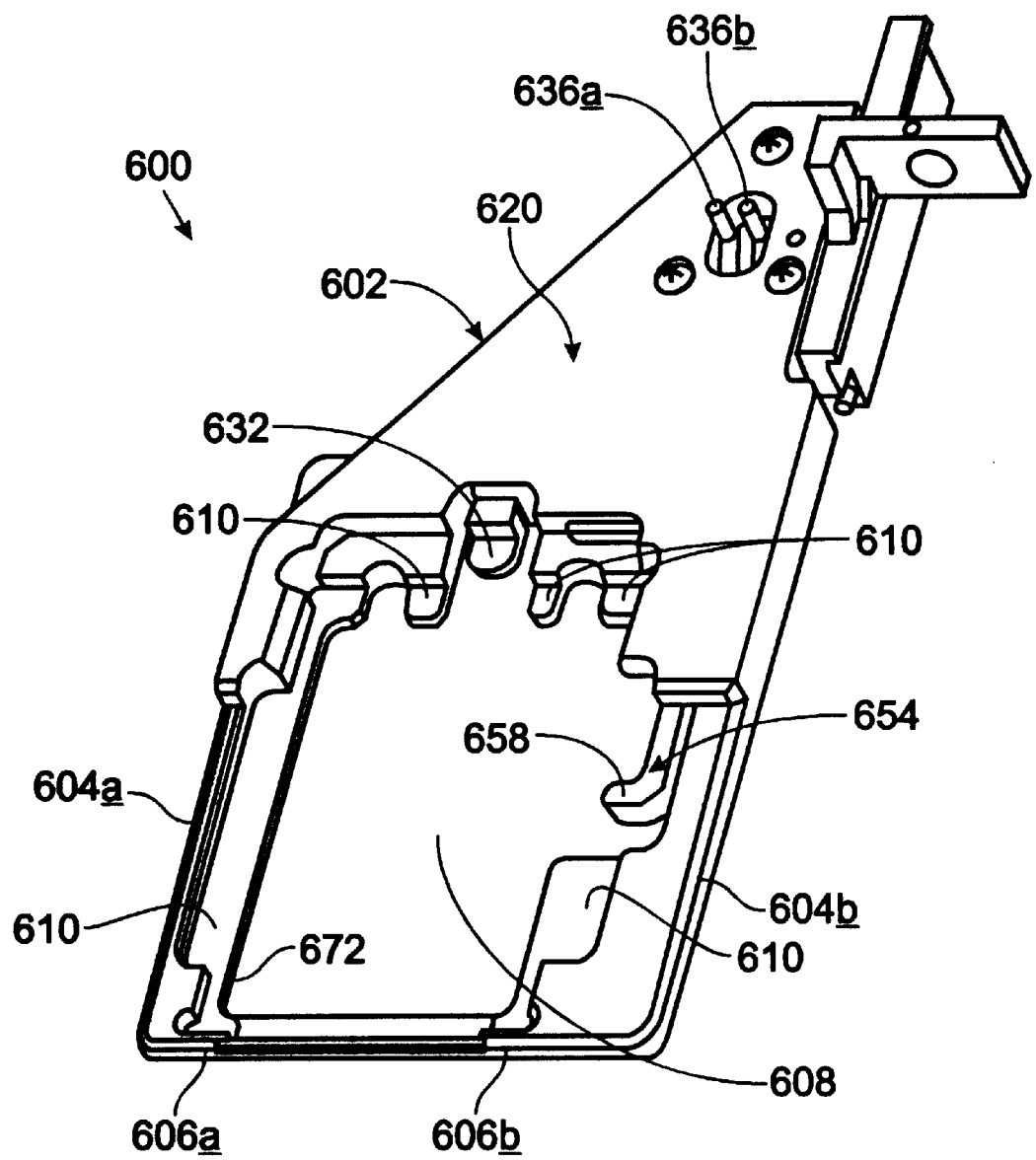
FIG. 22a is a perspective view of the top of a transporter assembly according to a preferred embodiment of the present invention.

FIGS. 22a–b show a stage, which generally comprises any mechanism for supporting a composition for analysis by the analyzer. In analyzer 50, the stage takes the form of a transporter 600.

Transporter 600 includes a transporter body 602 and substantially parallel first and second transporter flanges 604a,b that extend outward from transporter body 602. First and second transporter flanges 604a,b terminate in first and second transporter extensions 606a,b that turn in toward one another without contacting one another. Transporter body 602, flanges 604a,b, and extensions 606a,b lie substantially in a plane and define a transporter cavity 608 that is larger than any sample containers which the transporter is intended to support. The shape of this cavity is chosen to accommodate the shape of the preferred sample containers. In analyzer 50, cavity 608 is substantially rectangular to accommodate substantially rectangular sample containers, such as microplates. In analyzer 50, long sides of the rectangular sample container are positioned against flanges 604a,b.

Transporter shelves 610 along portions of body 602, flanges 604a,b, and extensions 606a,b form a structure that supports the bottom of the sample container. Other support mechanisms, such as pins or pegs, also could be employed instead of or in addition to shelves.

The transporter also includes an automatic sample container positioning mechanism 620 for precisely and reproducibly positioning sample containers within the cavity 608. Mechanism 620 includes Y and X axis positioning arms 622a,b that contact the sample container to control its Y and X position, respectively. Here, a Y axis is defined as generally parallel to transporter flanges 604a,b, and an X axis is defined as perpendicular to the Y axis and generally parallel to transporter extensions 606a,b. Other coordinate systems also can be defined, so long as they include two non-colinear directions.

Y-axis positioning anm 622a lies substantially within channel 624 in body 602. Y-axis positioning aim 622a includes a rod 626a, which is bent at substantially right angles to form thlee substantially coplanar and equal-lengilhed segments. A first end segment 628a of rod 626a terminates near cavity 608 in a bumper tab 630a for engaging a sample container. First end segment 628a is inserted into a bumper 632. A second end segment 634a of rod 626a terminates away from cavity 608 in an actuator tab 636a for controlling movement of arm 622a. Actuator tab 636a is bent away from body 602. First and second end segments 628a, 634a are substantially parallel. A middle segment 638a of rod 626a connects the two end segments at their non-tabbed ends 640, 641. An X-axis biasing spring 642a is slipped over rod 638a and a first spring end 644 is held to second end segment 634a of rod 626a by a clamping-type retaining ring 670a. A second spring end 648 rests against a rod bearing 671. The Y-axis biasing spring extends substantially parallel to first and second end segments 628a, 634a. The force from spring 642a is transmitted to rod 626a by the clamping action of retaining ring 670a.

X-axis positioning arm 622b also lies substantially within channel 624 in body 602 and is similar to Y-axis positioning arm, except that (1) first end segment 628b is longer and middle segment 638b is shoiler in rod 626b of the X-axis positioning arm than in rod 626a of the Y-axis positioning arm, (2) first end segment 628a terminates in a lever tab 630b in the X-axis positioning arm rather than in bumper 632 in the Y-axis positioning arm, and (3) the two rods bend in opposite directions between first end segments 638a,b and second end segments 634a,b.

X-axis positioning arm 622b is connected via lever tab 630b to an X-axis positioning lever 654 that lies along transporter flange 604b. X-axis positioning lever 654 includes two functional lever projections 656, 658 and is pivotally mounted about a lever pivot axis 659 to transporter 600 near the intersection of body 602 and flange 604b. A first lever projection 656 is substantially perpendicular to flange 604b and abuts lever tab 630b on X-axis positioning aim 622b for actuating the positioning lever. A second lever projection 658 also is substantially perperdicular to flange 604b and includes an edge 660 for contacting a sample container.

Transporter 600 functions as follows. For loading, the transporter occupies a loading position substantially outside a housing, as shown in FIG. 24. In this position, actuator tabs 636a,b abut actuator bar 670, biasing springs 642a,b are compressed, and bumper 632 and second projection 658 having edge 660 are pulled out of cavity 608. A person, robot, or mechanical stacker then can place a sample container into cavity 608 so that the bottom of the sample container rests on transporter shelves 610. Cavity 608 is larger than the sample container to facilitate this placement and to accommodate variations in sample container size.

For reading, the transporter must deliver the sample container to an examination site inside the housing. In this process, the transporter moves parallel to second end segments 634a,b and actuator tabs 636a,b disengage actuator bar 670. Biasing spring 642a pushes Y-axis positioning airn 622a toward cavity 608. Bumper 632 engages the sample container and pushes it away from body 602 until it abuts extensions 606a,b. Biasing spring 642b pushes X-axis positioning ann 622b toward cavity 608. Edge 660 of second projection 658 engages the sample container and pushes it away from flange 604b until it abuts flange 604a.

Under the action of both positioning arms, the sample container is precisely and reproducibly positioned (registered) against a reference comer 672 within cavity 608. Biasing springs 642a,b can be chosen to have different strengths, so that the X-Y positioning action is performed less or more forcefully. In analyzer 50, middle segment 638b and first lever projection 656 of positioning lever 654 can be varied in length to cause registration to occur first in the X-axis or first in the Y-axis. For example, reducing the length of middle segment 638b and reducing the length of projection 656 will cause registration to occur first in the X-axis.

As long as the microplate is placed in any position on the lower guide shelves, it can be adjusted into place by the automatic microplate positioning mechanism. A sensor (not shown) detects the presence of the sample container. The instrument can either be configured automatically to read the microplate once the sensor detects its presence or to signal the system controller through the RS-232 port that a microplate has been received and it is ready to accept a command to begin reading.

Positioning lever 654 and bumper 632 are retracted when body 602 of the automatic microplate positioning transporter is moved to the eject position by the X,Y stage. Thus, the microplate is placed on transporter shelf 610 only when the lever and bumper are retracted. Two springs 642a,b are attached to the rods, which run along the length of the transporter body and end perpendicular to the body. When the transporter is moved to the eject position, the two perpendicular ends of the rods encounter actuator bar 670, which consists of a rectangular structure located above and parallel to the body. The stop prevents the two perpendicular ends of the actuators, and thus the actuators, from moving with the transporter body. This causes the two springs to contract, changing the position of the transporter arms and increasing the amount of room for the microplate. The microplate can then be placed on the guide shelf of the body. When the body of the automatic microplate positioning transporter is moved back away from the stop, the two perpendicular ends of the actuators are no longer blocked, which allows the actuators, springs, and transporter arms to move into their original position. The expansion of the springs pushes the microplate into the exact position as defined by the reference corner.

Figure 23:
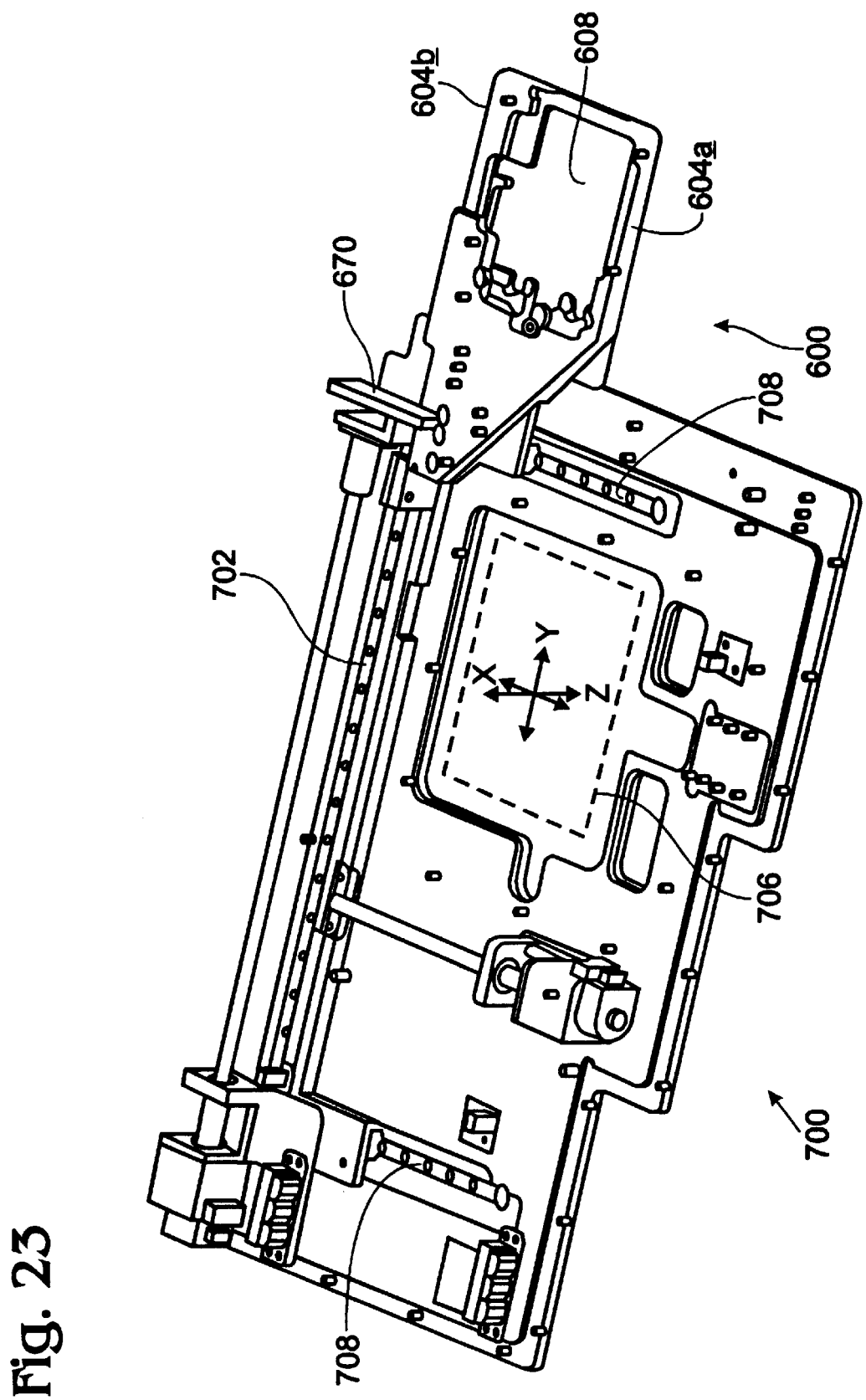
FIG. 23 is a perspective view of a base and drive mechanisms for moving transporter along X and Y axis relative to the base.

FIG. 23 shows a perspective view of transporter 600 mounted on base platform 700 with drive mechanisms for moving transporter 600 between loading and examination positions. As previously described, transporter 600 includes flanges 604a,b defining cavity 608 for receiving and gripping a microplate (not shown). A drive mechanism is provided for moving transporter 600 along a first track 702, relative to the Y-axis, from loading position 704 to examination position 706. Once transporter 600 reaches the examination position, an additional drive mechanism can be actuated to move transporter 600 along a second track 708 relative to the X-axis. In operation, a microplate is loaded in transporter 600 at the loading position. Transporter 600 is driven to the examination position by Y-axis drive mechanism. X and Y drive mechanisms then operate together to align selected microplate wells with the Z-axis, along which a sensed volume is defined by optical components contained in one or both of top and bottom optics heads positioned above and below base 700, respectively.

Exterior Features

The optical system and other components of analyzer 50 are maintained in a housing, both for organization and for protection. FIG. 24 shows housing 800 for analyzer 50, as well as the locations of important optical components within housing 800. Housing 800 is substantially rectangular and includes light-tight exterior top wall 802, side walls 803a–d, and bottom walls 804 that reduce background in luminescence measurements. The walls may include vents 806 to facilitate air flow through the analyzer and a transporter port 807 for sample input/output. Housing 800 also may include feet 808 to support the analyzer and to permit air flow between the analyzer and any support structure on which the analyzer is placed. Analyzer 50 is substantially automated and is designed so that user interactions occur primarily through control panel 810 and input/output panel 812 that support a variety of input/output functions. Transporter/stage 814 and optional sample feeder 816 are used for support sample input/output.

Control panel. The control panel generally comprises any interface used for direct input/output functions. This control panel may be integrated into the analyzer, or it may be a separate unit that can be positioned away fiom the analyzer or affixed to the analyzer at one or more locations. The control panel also may include more than one unit, each dedicated to different input/output functions or to use at different locations.

The control panel may be used in conjunction with a host computer for a variety of input/output functions. For example, the control panel may be used to input commands, such as signals to start and stop the instrument. Similarly, the control panel may be used to display output information, such as instrument status, instrument diagnostics, measurement results, and other information generated by the analyzer in different assay modes. The control panel is especially useful for automated operations that require manual user intervention.

An enlarged isolated view of control panel 810 of analyzer 50 is shown in FIG. 25. Control panel 810 is a separate unit that affixes to the analyzer at any one of a plurality of locations. Control panel 810 is substantially L-shaped, with substantially perpendicular inner surfaces 830a,b that mate with adjacent substantially perpendicular walls of the analyzer including top wall 802 and one of side walls 803a–d. In its preferred orientation, control panel 810 is mounted so that front face 832 is substantially parallel with one of side walls 803a–d of analyzer 50. Front face 832 includes a gas-plasma display 834, keypad 836, and indicator lights 838. Control panel 810 also may include additional and/or alternative components, and their relative organization may deviate from that shown in the drawings and discussed below. Gas-plasma display 834 is located in the upper center of front face 832 and is used to provide messages regarding instrument status. Additional displays and/or alternative display foimats, such as light-emitting diodes (LEDs) and liquid ciystal displays (LCDs), also may be used.

Keypad 836 is located below and to the right of gas-plasma display 834 and includes four keys. A "start" key 840 initiates the sample-reading process. A "load/eject" key 842 loads or ejects a sample container, such as a microplate, depending upon the current status of the instrument. A "reset" key 844 reinitializes the instrument, sending motors to their home positions and turning off the audible alarm. A "status" key 846 alters the state of the continuous lamp or activates reverse stack. Additional keypads and additional and/or alternative keys also may be employed. Alternative methods of data entry, such as a computer mouse or touch screen, also may be employed.

Indicator lights 838 are located to the left of the display and keypad. A "power" light 848 indicates that power is being supplied to the instrument. A "service" light 850 indicates that a service procedure is needed, such as changing a lamp. A "fault" light 852 indicates that a critical fault has occurred, which is a fault that requires intervention by an operator. Additional and/or alternative indicator lights also may be provided.

Control panel 810 also may include audio signals. For example, an audible alarm within the interior of control panel 810 may sound in the event of a critical fault. Alternative audio signals, such as prerecorded or synthesized voice messages, also may be used.

Control panel 810 may be moved between at least two control-panel mounting locations 854a,b on the instrument. Such flexible positioning permits acommands to be entered and status information, diagnostic information, measurements, and other information to be read from multiple positions. Flexible positioning is especially convenient when one or more sides of the analyzer are blocked due to analyzer placement or nearby peripherals. Alternatively, it permits two or more control panels to be connected at once, increasing convenience and flexibility.

The control panel includes two connector prongs (not shown), which can be mated with two RS-232 serial ports (not shown) on analyzer 50. These ports are connected through two RS-232 cables to a host computer, allowing the computer to communicate with the control panel.

Input/output panel. The input/output panel generally comprises any ports used for basic input/output functions. These include ports for providing and controlling power input to the analyzer, and for inputting and outputting data and commands. Components of the input/output panel may be collected for convenience in one location or positioned at various locations on the analyzer.

An enlarged isolated view of control input/output panel 812 is shown in FIG. 26. In analyzer 50, input/output panel 812 includes a power switch 870, power entry module 872, auxiliary port 874, and two RS-232 serial ports 876. Power switch 870 is located in the left center of the panel and is used to actuate analyzer 50. Power entry module 872 is located below the power switch and is used to supply power to analyzer 50; power arrives via a standard electrical cord 878 that may be plugged into a wall socket. Auxiliary port 874 and serial ports 876 are located above and to the right of the power entry module and are used for input/output. These ports provide flexibility, because they permit the analyzer to communicate with several different peripherals. Additional power entry modules and additional and/or alternative communication ports for input/output in alternative foimats and positions also may be used. A model/regulatory label 880 containing written information regarding the analyzer is provided below power entry module 872 on the input/output panel.

Sample feeder

The analyzer may include a sample feeder, which generally comprises any mechanism for automatic processing of multiple sample containers. The sample feeder enhances convenience by reducing the amount of human intervention required to run the analyzer. The sample feeder also enhances throughput by reducing the amount of time required to process multiple microplates.

As shown in FIG. 24, sample feeder 890 is integrated into the analyzer. Sample feeder 890 includes an input bin 892 for holding microplates to be read, an output bin 894 for holding microplates that have been read, and a direct transporter access bin 896 to input or output microplates by bypassing the input and output bins. Input and output bins 892, 894 accommodate input and output microplate magazines (not shown) that hold and organize stacks of microplates before and after reading, respectively. Microplate magazines can be used with other robotics to dispense, wash, and read without restacking microplates. Direct transporter access bin permits a user to access the transporter to deliver or remove a microplate without removing the magazines.

Sample feeder 890 operates as follows. Before reading, a robot (1) removes a microplate from the bottom of the stack of microplates in the input bin, (2) transports the microplate to the direct transporter access bin, and (3) transfers the microplate to the transporter. After reading, the robot (1) takes the microplate from the transporter, (2) transports the microplate to the output bin, and (3) transfers the microplate to the bottom of the output stack in the output bin.

Sample feeder 890 is designed to be flexible. Input and output bins 892, 894 can accommodate a variety of commercially available microplates and microplate magazines and are large enough to allow microplates to be placed in them by a robot. Suitable microplates typically have 96 or 384 wells, but other configurations also can be ccommodated. Preferred 96-well microplates include COSTAR black flat-bottom model #3915 and a DYNATECH MicroFluor round-bottom micoplate; preferred 384-well microplates include COSTAR black model #3710 and PACKARD white model #6005214. Suitable microplate magazines can accommodate 10–100 microplates. FIG. 1 shows magazines that can accommodate 20 microplates. Preferred microplate magazines include the TITERTEK S20 magazine.

Sample feeder 890 includes a process compression feature that reduces the number of passes that the robot must make to load and unload microplates on the transporter. This feature exploits the separate input (landing) and output (pickup) positions. The robot can pick up microplates that have been read and place them in the output bin. Microplates can be loaded into the direct transporter access bin by the robot and then the robot can go directly to the output bin to pick up the next microplate. Thus, one robot movement with the process compression feature replaces two separate robot movements without the feature. Finally, the automatic sample feeder requires only two motors to provide all mechanical functions with high throughput (~5 seconds for load and unload time). The robot can deposit a microplate in the input stack or the transporter and pick up a microplate after it is read from either the transporter or from the output stack.

In robotic operation, the feeder can reduce robot hand travel by providing separate landing (input) and pickup (output) positions. The system is designed to allow a microplate to be inserted and another removed by a robot in one pass, a feature known as process Compression.

Sample feeder 890 may include a barcode reader 898 that can be used automatically to identify labeled microplates. Barcode reader 898 can be placed in either of the positions shown in boxes in dashed lines in sample feeder 890. Barcode reader 898 reads barcodes mounted on the long edge or the short edge of microplates. Barcodes are read while the feeder moves the microplate from the input magazine into the light-tight enclosure. Barcodes cannot be read when microplates are delivered directly to the transfer position. Barcode reader 898 can be programmed to decode a variety of symbologies, including SPC (EAN, JAN, UPC), Code 39 (3–43 digits), Codabar (3–43 digits), Standard 2 of 5 (3–43 digits), Interleaved 2 of 5 (4–43 digits), Code 93 (5–44 digits), and MSI-Plessey (4–22 digits), among Others Information obtained from the barcode can be used for a number of different purposes. For example, the barcode string can be used to name the report file. The barcode can also be used to convey instructions to the analyzer relating to required changes in assay mode or optics configuration.

The above description elaborates on the general architecture of the invention while also describing preferred embodiments. Other related embodiments are possible and may be desirable for specific applications. For example, it may be desirable to commercialize only a portion of the preferred embodiment to meet the needs of different customers or specific markets. Also, the preferred embodiments provide for an expandable architecture wherein light sources and detectors can be added as required to provide new assay modalities, or to take advantage of new types of light sources and photodetectors, as they become commercially available. For example, blue LEDs have become commercially available only in the last few years, and blue laser diodes are expected to become commercially available within the next few years. The architecture of the invention is designed to be flexible so as to allow incorporation of newly commercialized technology with the goal of making such technology available to high-throughput screening labs at the earliest possible date.

Another alternative embodiment may include a plurality of confocal detection systems mounted in a linear array or matrix. A linear array of 8 or 12 confocal detectors may be used with one or more light sources and 8 or 12 photodetectors to simultaneously detect an entire row or column of a 96 well microplate. The same detectors could also be used to read 384 or 1536 well plates with the proper aperture installed since the well-to-well pitch of the higher density plates are evenly divisible into that of the 96 well plate. In another example, the confocal detection systems could be mounted in an n-by-m array and could also detect one or more plate formats.

We claim:

1. An apparatus for detecting light transmitted from a composition, the apparatus comprising:
   a stage for supporting a composition in an examination site, the composition being contained in a spatial volume lying between boundary interfaces located at different points along a Z-axis, wherein the Z-axis is substantially perpendicular to tie stage;
   an automated registration device that automatically brings successive compositions and the examination site into register for successive analysis of the compositions;
   a light source positioned to deliver light to the composition in the examination site;
   a detector positioned to receive light transmitted from the composition in the examination site;
   an optical relay structure located between the light source and the detector, the optical relay structure being capable of transmitting light substantially exclusively from a sensed volume of the composition, wherein the sensed volume is spaced substantially away from at least one of the boundary interfaces of the composition; and
   a Z-axis optical adjustment device that automatically adjusts positions of the sensed volume along the Z-axis between and spaced away from the boundary interfaces.

2. The apparatus of claim 1, wherein the optical relay structure includes confocal optics elements substantially contained within an optics head positioned above or below the stage, the Z-axis optical adjustment device including a drive mechanism that moves the optics head relative to the Z-axis.

3. The apparatus of claim 1, wherein X, Y-axes are defined perpendicular to each other, perpendicular to the Z-axis and parallel to the stage, further comprising an X, Y-axes adjustment device that automatically adjusts the relative positions of the sensed volume and the composition along the X and Y axes.

4. The apparatus of claim 3, wherein the X, Y-axes adjustment device can be programmed to convey successive compositions to the examination site.

5. The apparatus of claim 4, wherein the successive compositions are contained in wells of a microplate.

6. The apparatus of claim 1, wherein the sensed volume is spaced substantially away from all the boundary interfaces.

7. The apparatus of claim 1, wherein the sensed volume has a waist region in a sample plane, and a Z-pick-up, the diameter of the waist region being approximately half the dimension of the Z-pick-up.

8. The apparatus of claim 1, wherein the optical relay structure includes an aperture substantially centered about the Z-axis and contained in an image plane conjugate to a sample plane intersecting the sensed volume.

9. The apparatus of claim 1, wherein the apparatus is capable of detecting light in at least two of the following types of assays: luminescence intensity, photoluminescence polarization, chemiluminescence, photoluminescence lifetime absorbance, luminescence resonance energy transfer, and luminescence imaging.

10. The apparatus of claim 1, wherein the detector detects light of longer wavelength than the light delivered to the composition from the light source.

11. The apparatus of claim 1, further comprising an automated registration device controller for preprogramming the relative movement into registration of successive compositions and the examination site.

12. The apparatus of claim 1, wherein the light source is a lamp, or a light-emitting diode, or a laser, or a flash lamp, or a particle accelerator.

13. The apparatus of claim 1, wherein the light source is one of a plurality of light sources positioned at a source station, and further comprising a switching mechanism for interchangeably connecting different light sources to the optical relay structure for different applications.

14. The apparatus of claim 13, wherein the switching mechanism includes a shuttle having one side connected to a fiber optic element leading toward the stage, and a second side substantially facing the light sources, the shuttle being movable relative to the light sources, so that different light sources can be selectively transmitted through the fiber optic element to a composition at the examination site.

15. The apparatus of claim 13, further comprising a filter wheel connected to the source station, the filter wheel containing a plurality of filters and being rotatable about a rotational axis so that a given filter can be interchangeably interposed between different light sources and the optical relay structure.

16. The apparatus of claim 1, wherein the detector is a photomultiplier tube, or a photodiode, or a charge-coupled device.

17. The apparatus of claim 1, wherein successive compositions are held in adjacent wells in a microplate.

18. The apparatus of claim 17, wherein the number of wells in the microplate is 96, or 384, or 1536.

19. The apparatus of claim 1, wherein the optical relay structure simultaneously transmits light to the detector from compositions contained in a plurality of microplate wells.

20. The apparatus of claim 1, wherein the optical relay structure delivers light from the light source at an angle relative to the Z-axis exceeding the critical angle for establishing an evanescent field in the composition.

21. The apparatus of claim 1, wherein the optical relay structure delivers light from the light source at an angle relative to the Z-axis below the critical angle for establishing an evanescent field in the composition.

22. The apparatus of claim 1, wherein the sensed volume is diffraction limited.

23. The apparatus of claim 1, wherein the light source produces high-intensity, high-color temperature light.

24. The apparatus of claim 23, wherein the light source is a xenon arc lamp.

25. The apparatus of claim 1, wherein the automated registration device includes a transporter having a mechanism that releasably grips and moves a sample container to and from the examination site.

26. The apparatus of claim 25, wherein the transporter is dimensioned to grip and carry a microplate.

27. The apparatus of claim 25, wherein the transporter is the stage.

28. The apparatus of claim 27, further comprising
a housing, the transporter being movable along a path running between a loading position and the examination site, the loading position being substantially outside the housing, so that compositions can be easily loaded on and unloaded from the transporter when the transporter is in the loading position, and the transporter can deliver compositions to and from the examination site inside the housing before and after analysis.

29. The apparatus of claim 28, further comprising
a stacking unit mounted next to the loading position outside the housing, the stacking unit being configured to hold a plurality of sample containers, and to feed sample containers to the transporter one at a time.

30. The apparatus of claim 29, wherein the sample containers are croplates.

31. The apparatus of claim 27, wherein the transporter is open in the enter so that when the transporter is in the examination site, light can be transmitted rom below the stage to a composition in the examination site.

32. The apparatus of claim 1, wherein the optical relay structure includes a first aperture and a first lens positioned along a light path between the light source and the examination site or between the detector and the examination site.

33. The apparatus of claim 32, wherein the optical relay structure includes a second aperture and a second lens, the first aperture and the first lens being positioned along a light path between the light source and the examination site, the second aperture and the second lens being positioned along a light path between the detector and the examination site so that light is transmitted substantially exclusively to and from the same sensed volume in a composition at the examination site.

34. The apparatus of claim 32, wherein the optical relay structure cludes at least one fiber optic element, the first aperture being defined by the dimension of an end of the fiber optic element.

35. The apparatus of claim 32, wherein the first aperture is defined in a ask structure at an end of a fiber optic element.

36. The apparatus of claim 32, wherein the optical relay structure includes a second aperture, the first and second apeitures having different dimensions, and an aperture switching mechanism for interchangeably positioning a selected aperture in the light path leading to or from a sensed volume in a composition at the examination site, so that the size of the sensed volume can be altered by switching between the first and second apertures.

37. The apparatus of claim 32, wherein the diameter of the first aperture is adjustable.

38. The apparatus of claim 32, wherein the first aperture and the first lens are contained in a first optics head positioned near the stage.

39. The apparatus of claim 38, wherein the first optics head is positioned above the stage.

40. The apparatus of claim 38, wherein the first optics head is positioned below the stage.

41. The apparatus of claim 38, wherein the first optics head has a light entrance port optically connected to the light source, and a light exit port optically connected to the detector, so that illumination and detection of light transmitted from a composition in the examination site can be carried out fiom the same side of the stage.

42. The apparatus of claim 41, wherein the light entrance port and the light exist port are configured to transmit light in directions that are substantially perpendicular to each other.

43. The apparatus of claim 42, wherein the first optics head includes a planar beam splitter oriented at 45 degree angles to the directions of light transmission.

44. The apparatus of claim 39, wherein the optical relay structure includes a second optics head positioned below the stage, each optics head having a light entrance port optically connected to the light source, and a light exit port optically connected to the detector, and a switch control mechanism capable of interchangeably configuring any one of the following light transmission routes to and from a sensed volume in a composition located at the examination site: (a) top-illumination and top-detection, (b) top-illumination and bottom-detection, (c) bottom-illumination and top-detection, and (d) bottom-illumination and bottom-detection.

45. An apparatus for detecting light transmitted from a composition, the apparatus comprising:
- a stage for supporting a composition in a spatial volume having boundary interfaces located along surfaces in a microplate well;
- a light source positioned to deliver light from the light source into the composition;
- a detector;
- an optical relay structure that is capable of transmitting light substantially exclusively from a sensed volume of the composition to the detector, wherein the sensed volume is spaced substantially away from the boundary interfaces of the composition; and
- a Z-axis optical adjustment device, wherein a Z-axis is defined perpendicular to the stage, the Z-axis optical adjustment device that automatically adjusts positions the sensed volume along the Z-axis in the composition between and spaced away from the boundary interfaces.

46. The apparatus of claim 45, wherein X, Y-axes are defined perpendicular to each other, perpendicular to the Z-axis and parallel to the stage, further comprising an X, Y-axes adjustment device that automatically adjusts the relative positions of the sensed volume and the composition along the X and Y-axes.

47. The apparatus of claim 45, wherein a Z-axis is defined substantially perpendicular to the stage of an examination site, the optical relay structure including an aperture substantially centered about the Z-axis and contained in an image plane conjugate to a sample plane intersecting the sensed volume.

48. The apparatus of claim 45, wherein the apparatus is capable of detecting light in at least two of the following types of assays: luminescence intensity, photoluminescence polarization, cheiniluminescence, photoluminescence lifetime absorbance, luminescence resonance energy transfer, luminescence imaging.

49. The apparatus of claim 45, wherein the detector detects light of longer wavelength than the light delivered to the composition from the light source.

50. The apparatus of claim 45, wherein the light source is a lamp, or a light-emitting diode, or a laser, or a flash lamp, or a particle accelerator.

51. The apparatus of claim 45, wherein the detector is a photomultiplier tube, or a photodiode, or a charge-coupled device.

52. The apparatus of claim 45, wherein the microplate well is contained in a microplate, wherein the number of wells in the microplate is 96, or 384, or 1536.

53. The apparatus of claim 45, wherein the microplate well containing the composition is located at an examination site, the optical relay structure including a first aperture and a first lens positioned along a light path between the detector and the examination site.

54. The apparatus of claim 45, wherein the optical relay structure includes a second aperture and a second lens positioned along a light path running between the light source and the examination site.

55. The apparatus of claim 53, wherein the optical relay structure includes at least one fiber optic element, the first aperture being defined by the dimension of an end of the fiber optic element.

56. The apparatus of claim 53, wherein the first aperture is defined in a mask structure at an end of a fiber optic element.

57. The apparatus of claim 53, wherein the optical relay structure includes a second aperture, the first and second apertures having different dimensions, and an aperture switching mechanism for interchangeably positioning a selected aperture in the light path leading to or from a sensed volume in a composition at the examination site, so that the size of the sensed volume can be altered by switching between the first and second apertures.

58. The apparatus of claim 53, wherein the first aperture and the first lens are contained in a first optics head positioned near the stage.

59. The apparatus of claim 58, wherein the first optics head is positioned above the stage.

60. The apparatus of claim 58, wherein the first optics head is positioned below the stage.

61. The apparatus of claim 58, wherein the first optics head has a light entrance port optically connected to the light source, and a light exit port optically connected to the detector, so that illumination and detection of light transmitted from a composition in the examination site can be carried out fiom the same side of the stage.

62. The apparatus of claim 61, wherein the light entrance port and the light exit port are configured to transmit light in directions that are substantially perpendicular to each other.

63. The apparatus of claim 62, wherein the first optics head includes a planar beamsplitter oriented at 45-degree angles to the directions of light transmission.

64. The apparatus of claim 59, wherein the optical relay structure includes a second optics head positioned below the stage, each optics head having a light entrance port optically connected to the light source, and a light exit port optically connected to the detector, and a switch control mechanism capable of interchangeably configuring any one of the following light transmission routes to and from a sensed volume in a composition located at the examination site: (a) top-illumination and top-detection, (b) top-illumination and bottom-detection, (c) bottom-illumination and top-detection, and (d) bottom-illumination and bottom-detection.

65. An apparatus for detecting light transmitted from a composition, the apparatus comprising:
- a stage for suppoing a composition in a spatial volume having boundary interfaces located along surfaces in a microplate well;
- a light source;
- an optical relay structure that is capable of delivering light from the light source substantially exclusively to a sensed volume of the composition, wherein the sensed volume is spaced substantially away from the boundary interfaces of the composition;
- a detector positioned to receive light transmitted from the sensed volume of the composition; and
- a Z-axis optical adjustment device, wherein a Z-axis is defined perpendicular to the stage, the Z-axis optical adjustment device that automatically adjusts positions of the sensed volume along the Z-axis between and spaced away from the boundary interfaces of the composition.

66. An apparatus for detecting photoluminescence emitted by a sample, the apparatus comprising:
- a stage configured to hold a microplate having an array of sample wells;
- a light source located at one end of a first light path leading toward the stage and configured to deliver light to induce photoluminescence in a sample contained within boundary interfaces in at least one of the sample wells along a Z-axis perpendicular to the stage;
- a detector located at one end of a second light path leading toward the stage and configured to detect photoluminescence emitted by the sample;

a confocal optics element operatively positioned along the first light path or the second light pat, and configured substantially to prevent light from focusing outside a pre-selected sensed volume inside the sample, or configured substantially to prevent detection of photoluminescence originating outside the sensed volume; and an optical adjustment device that automatically adjusts positions of the sensed volume along the Z-axis inside the sample between and spaced away from the boundary interfaces.

67. An apparatus for detecting luminescence emitted by a sample, the apparatus comprising:

a stage configured to hold a sample inside boundary interfaces along a Z-axis perpendicular to the stage at an examination site for analysis;

an alignment device configured to adjust the relative positions of the stage and the examination site, so that the sample and the examination site can be brought into alignment before detection of luninescence, and removed from alignment after such detection;

an alignment device controller configured automatically to control the alignment device, so that successive samples can be thought into alignment with the examination site for detection of luminescence;

an optical focusing structure configured sequentially to focus luminescence from the portion of the sample positioned in a sample plane into a series of image planes, wherein the image planes include at least one intermediate image plane and one terminal image plane;

a detector configured to detect luminescence emitted by the sample, wherein the detector is positioned substantially in the terminal image plane;

an emission confocal optics element configured substantially to prevent detection of luminescence originating outside a sensed volume intersecting the sample plane, wherein the emission confocal optics element is positioned between the sample and the detector substantially in an intermediate image plane; and a sensed volume positioning mechanism that automatically adjusts positions of the sensed volume along the Z-axis inside the sample between and spaced away from the boundary interfaces.

68. The apparatus of claim 67, wherein the optical focusing structure includes at least one lens positioned along a light path leading from the sample plane to the detector.

69. The apparatus of claim 67, wherein the emission confocal optics element defines an aperture.

70. The apparatus of claim 69, wherein the aperture is adjustable.

71. The apparatus of claim 67, further comprising:

a light source configured to deliver light to induce luminescence in the sample; and an excitation confocal optics element configured substantially to prevent light from the light source from focusing outside the portion of the sample plane contained in the sensed volume;

wherein the excitation confocal optics element is positioned substantially in an intermediate image plane located between the light source and the sample; and wherein there are at least two intermediate image planes, with the emission confocal optics element and the excitation confocal optics element positioned in different image planes.

72. A method of detecting light transmitted from a composition, the method comprising:

automatically bringing into register a succession of compositions and an examination site for successive analysis of the compositions, wherein each composition is contained between top, bottom, and side boundary interfaces located at different points along a Z-axis;

transmitting light into a composition at the examination site;

autmatically adjusting the position of a sensed volume along the Z-axis between and spaced away from the boundary interfaces; and detecting light substantially exclusively from the sensed volume in the composition.

73. A high-throughput method of detecting light transmitted from a succession of samples, the method comprising:

automatically and sequentially aligning a succession of samples with a Z-axis at an examination site, a sample being contained within boundary interfaces;

for each sample, focusing light originating from the waist region of a sensed volume into a series of image planes, beginning with at least one intermediate image plane and terminating with a terminal image plane;

positioning a detector in the terminal image plane to detect light transmitted by the sample;

positionng an emission confocal optics element in an intermediate image plane, wherein the emission confocal optics element is configured substantially to prevent detection of light originating outside the sensed volume; and automatically adjusting the position of the sensed volume along the Z-axis inside the sample between and spaced away from the boundary interfaces.

74. The high-throughout method of claim 73, further comprising:

positioning a light source to induce emission of light by the sample; and positioning an excitation confocal optics element in an intermediate image plane, wherein the excitation confocal optics element is configured substantially to prevent light from the light source from focusing outside the waist region of the sensed volume.

75. The method of claim 72 further comprising the step of spacing the sensed volume away from at least one of the boundary interfaces.

76. The method of claim 72 further comprising the step of spacing the sensed volume away from both of the top and bottom boundary interfaces.

77. The apparatus of claim 44, wherein each optics head is independently adjustable along the Z-axis.

* * * * *

UNITED STATES PATENT AND TRADEMARK OFFICE
CERTIFICATE OF CORRECTION

PATENT NO.   : 6,071,748
DATED        : June 6, 2000
INVENTOR(S)  : Douglas N. Modlin It is certified that error appears in the above-identified patent and that said Letters Patent is hereby corrected as shown below:

Column 26,
Line 8, delete "tie" and insert -- the -- therefor.

Column 28,
Line 2, delete "croplates" and insert -- microplates -- therefor.
Line 4, delete "enter" and insert -- center -- therefor.
Line 5, delete "rom" and insert -- from -- therefor.
Line 21, delete "cludes" and insert -- includes -- therefor.
Line 25, delete "ask" and insert -- mask -- therefor.
Line 28, delete "apeitures" and insert -- apertures -- therefor.
Line 48, delete "fiom" and insert -- from -- therefor.
Line 50, delete "exist" and insert -- exit -- therefor.

Column 29,
Line 35, delete "cheiniluminescence" and insert -- chemiluminescence -- therefor.

Column 30,
Line 38, delete "suppoing" and insert -- supporting -- therefor.

Column 31,
Line 2, delete "pat" and insert -- path -- therefor.
Line 19, delete "luninescence" and insert -- luminescence -- therefor.
Line 24, delete "thought" and insert -- brought -- therefor.

Column 32,
Line 25, delete "a" and insert -- each -- therefor.

Signed and Sealed this

Twenty-first Day of May, 2002

Attest:

JAMES E. ROGAN
Attesting Officer    Director of the United States Patent and Trademark Office